US008388684B2

(12) United States Patent
Bao et al.

(10) Patent No.: US 8,388,684 B2
(45) Date of Patent: Mar. 5, 2013

(54) ARTIFICIAL DISC DEVICE

(75) Inventors: Qi-Bin Bao, Marquette, MI (US);
Jeffrey L. Trudeau, Marquette, MI (US); Brian Patrick Janowski, Marquette, MI (US); Matthew N. Songer, Marquette, MI (US); Hansen Yuan, Fayetteville, NY (US); Thomas S. Kilpela, Marquette, MI (US); Gregory Berrevoets, Skandia, MI (US)

(73) Assignee: Pioneer Signal Technology, Inc., Marquette, MI (US)

( * ) Notice: Subject to any disclaimer, the term of this patent is extended or adjusted under 35 U.S.C. 154(b) by 1510 days.

(21) Appl. No.: 10/692,468

(22) Filed: Oct. 22, 2003

(65) Prior Publication Data

US 2005/0033437 A1 Feb. 10, 2005

Related U.S. Application Data

(63) Continuation-in-part of application No. 10/282,620, filed on Oct. 29, 2002, now Pat. No. 7,001,433.

(60) Provisional application No. 60/382,758, filed on May 23, 2002.

(51) Int. Cl.
*A61F 2/44* (2006.01)
(52) U.S. Cl. ............... 623/17.14; 623/17.11; 623/17.15; 623/17.16
(58) Field of Classification Search ........................ None
See application file for complete search history.

(56) References Cited

U.S. PATENT DOCUMENTS

| 3,867,728 A | 2/1975 | Stubstad et al. |
| 3,875,595 A | 4/1975 | Froning |
| 3,975,778 A | 8/1976 | Newton, III |
| 4,021,382 A | 5/1977 | Stoy et al. |
| 4,081,402 A | 3/1978 | Levy et al. |
| 4,147,764 A | 4/1979 | Levy et al. |
| 4,309,777 A | 1/1982 | Patil |
| 4,349,921 A | 9/1982 | Kuntz |
| 4,650,490 A | 3/1987 | Figgie, III |
| 4,714,469 A | 12/1987 | Kenna |
| 4,759,766 A | 7/1988 | Buettner-Janz et al. |
| 4,759,769 A | 7/1988 | Hedman et al. |
| 4,863,476 A | 9/1989 | Shepperd |
| 4,863,477 A | 9/1989 | Monson |
| 4,917,704 A | 4/1990 | Frey et al. |
| 4,932,969 A | 6/1990 | Frey et al. |

(Continued)

FOREIGN PATENT DOCUMENTS

| CA | 2395609 | 2/2001 |
| CA | 2482403 | 10/2002 |

(Continued)

OTHER PUBLICATIONS

European Search Report dated Feb. 20, 2008, corresponding to European Patent Application No. 03738960.8-2310.

(Continued)

*Primary Examiner* — David Isabella
*Assistant Examiner* — Joshua Levine
(74) *Attorney, Agent, or Firm* — Fitch, Even, Tabin & Flannery LLP

(57) ABSTRACT

An artificial disc device for replacing a damaged nucleus is disclosed. In one form, the device may be inserted in components such that the device may be assembled within and retained by the natural annulus therein. In another form, the device may be inserted into the natural annulus in a collapsed or compressed state or arrangement and then be expanded within and retained by the annulus therein.

20 Claims, 15 Drawing Sheets

U.S. PATENT DOCUMENTS

| | | | |
|---|---|---|---|
| 4,936,848 A | 6/1990 | Bagby |
| 4,946,378 A | 8/1990 | Hirayama et al. |
| 4,997,432 A | 3/1991 | Keller |
| 5,002,576 A | 3/1991 | Fuhrmann et al. |
| 5,035,716 A | 7/1991 | Downey |
| 5,047,055 A | 9/1991 | Bao et al. |
| 5,071,437 A | 12/1991 | Steffee |
| 5,108,438 A | 4/1992 | Stone |
| 5,127,920 A | 7/1992 | MacArthur |
| 5,133,759 A | 7/1992 | Turner |
| 5,133,772 A | 7/1992 | Hack et al. |
| 5,147,404 A | 9/1992 | Downey |
| 5,171,281 A | 12/1992 | Parsons et al. |
| 5,176,710 A | 1/1993 | Hahn et al. |
| 5,192,326 A | 3/1993 | Bao et al. |
| 5,258,031 A | 11/1993 | Salib et al. |
| 5,258,043 A | 11/1993 | Stone |
| 5,273,742 A | 12/1993 | Gould et al. |
| 5,306,308 A | 4/1994 | Gross et al. |
| 5,306,309 A | 4/1994 | Wagner et al. |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Büttner-Janz et al. |
| 5,425,773 A | 6/1995 | Boyd et al. |
| 5,458,642 A | 10/1995 | Beer et al. |
| 5,458,643 A | 10/1995 | Oka et al. |
| 5,507,816 A | 4/1996 | Bullivant |
| 5,514,180 A | 5/1996 | Heggeness et al. |
| 5,522,899 A | 6/1996 | Michelson |
| 5,534,029 A | 7/1996 | Bao et al. |
| 5,549,679 A | 8/1996 | Kuslich |
| 5,556,431 A | 9/1996 | Büttner-Janz |
| 5,556,433 A | 9/1996 | Gabriel et al. |
| 5,562,736 A | 10/1996 | Ray et al. |
| 5,562,738 A | 10/1996 | Boyd et al. |
| 5,595,563 A | 1/1997 | Moisdon |
| 5,609,643 A | 3/1997 | Colleran et al. |
| 5,645,596 A | 7/1997 | Kim et al. |
| 5,645,597 A | 7/1997 | Krapiva |
| 5,658,336 A | 8/1997 | Pisharodi |
| 5,665,122 A | 9/1997 | Kambin |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,693,100 A | 12/1997 | Pisharodi |
| 5,702,450 A | 12/1997 | Bisserie |
| 5,716,416 A | 2/1998 | Lin |
| 5,728,762 A | 3/1998 | Reich et al. |
| 5,755,797 A | 5/1998 | Baumgartner |
| 5,755,798 A | 5/1998 | Papavero et al. |
| 5,782,832 A | 7/1998 | Larsen et al. |
| 5,824,093 A | 10/1998 | Ray et al. |
| 5,824,094 A | 10/1998 | Serhan et al. |
| 5,860,980 A | 1/1999 | Axelson, Jr. et al. |
| 5,865,845 A | 2/1999 | Thalgott |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,919,235 A | 7/1999 | Husson et al. |
| 5,964,807 A | 10/1999 | Gan et al. |
| 5,976,186 A | 11/1999 | Bao et al. |
| 5,980,572 A | 11/1999 | Kim et al. |
| 6,001,130 A | 12/1999 | Bryan et al. |
| 6,019,793 A | 2/2000 | Perren et al. |
| 6,022,376 A | 2/2000 | Assell et al. |
| 6,039,763 A | 3/2000 | Shelokov |
| RE36,758 E | 6/2000 | Fitz |
| 6,074,390 A | 6/2000 | Zucherman et al. |
| 6,093,205 A | 7/2000 | McLeod et al. |
| 6,093,207 A | 7/2000 | Pisharodi |
| 6,110,210 A | 8/2000 | Norton et al. |
| 6,127,597 A | 10/2000 | Beyer et al. |
| 6,132,465 A | 10/2000 | Ray et al. |
| 6,136,031 A | 10/2000 | Middleton |
| 6,139,579 A | 10/2000 | Steffee et al. |
| 6,143,031 A | 11/2000 | Knothe et al. |
| 6,146,422 A | 11/2000 | Lawson |
| 6,156,067 A | 12/2000 | Bryan et al. |
| 6,162,252 A | 12/2000 | Kuras et al. |
| 6,179,874 B1 | 1/2001 | Cauthen |
| 6,183,518 B1 | 2/2001 | Ross et al. |
| 6,187,048 B1 | 2/2001 | Milner et al. |
| 6,190,387 B1 | 2/2001 | Zucherman et al. |
| 6,206,924 B1 | 3/2001 | Timm |
| 6,224,630 B1 | 5/2001 | Bao et al. |
| 6,240,926 B1 | 6/2001 | Chin Gan et al. |
| 6,251,140 B1 | 6/2001 | Marino et al. |
| 6,264,695 B1 | 7/2001 | Stoy |
| 6,280,475 B1 | 8/2001 | Bao et al. |
| 6,283,968 B1 | 9/2001 | Mehdizadeh |
| 6,283,998 B1 | 9/2001 | Eaton |
| 6,315,795 B1 | 11/2001 | Scarborough et al. |
| 6,315,797 B1 | 11/2001 | Middleton |
| 6,348,071 B1 | 2/2002 | Steffee et al. |
| 6,352,557 B1 | 3/2002 | Ferree |
| 6,368,350 B1 * | 4/2002 | Erickson et al. ........... 623/17.14 |
| 6,371,990 B1 | 4/2002 | Ferree |
| 6,375,682 B1 | 4/2002 | Fleischmann et al. |
| 6,395,032 B1 | 5/2002 | Gauchet |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,544 B1 | 8/2002 | Ralph et al. |
| 6,428,575 B2 | 8/2002 | Koo et al. |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph et al. |
| 6,436,140 B1 | 8/2002 | Liu et al. |
| 6,436,141 B2 | 8/2002 | Castro et al. |
| 6,436,142 B1 | 8/2002 | Paes et al. |
| 6,436,146 B1 | 8/2002 | Hassler et al. |
| 6,440,168 B1 | 8/2002 | Cauthen |
| 6,440,170 B1 | 8/2002 | Jackson |
| 6,478,822 B1 | 11/2002 | Leroux et al. |
| 6,488,716 B1 | 12/2002 | Huang et al. |
| 6,508,839 B1 | 1/2003 | Lambrecht et al. |
| 6,517,580 B1 | 2/2003 | Ramadan et al. |
| 6,527,804 B1 | 3/2003 | Gauchet et al. |
| 6,540,785 B1 | 4/2003 | Gill et al. |
| 6,547,823 B2 | 4/2003 | Scarborough et al. |
| 6,562,047 B2 | 5/2003 | Ralph et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,592,624 B1 | 7/2003 | Fraser et al. |
| 6,602,291 B1 | 8/2003 | Ray et al. |
| 6,610,091 B1 | 8/2003 | Reiley |
| 6,679,915 B1 | 1/2004 | Cauthen |
| 6,682,562 B2 | 1/2004 | Viart et al. |
| 6,743,257 B2 | 6/2004 | Castro |
| 6,770,095 B2 | 8/2004 | Grinberg et al. |
| 6,783,550 B2 | 8/2004 | MacArthur |
| 6,793,678 B2 | 9/2004 | Hawkins |
| 6,899,716 B2 | 5/2005 | Cragg |
| 6,936,071 B1 * | 8/2005 | Marnay et al. ............. 623/17.15 |
| 7,001,433 B2 | 2/2006 | Songer et al. |
| 7,156,876 B2 | 1/2007 | Moumene et al. |
| 2001/0010021 A1 | 7/2001 | Boyd et al. |
| 2001/0012938 A1 | 8/2001 | Zucherman et al. |
| 2001/0016772 A1 | 8/2001 | Lee et al. |
| 2001/0016773 A1 | 8/2001 | Serhan et al. |
| 2001/0016776 A1 | 8/2001 | Zuckerman et al. |
| 2001/0020476 A1 | 9/2001 | Gan et al. |
| 2001/0027343 A1 | 10/2001 | Keller |
| 2001/0032019 A1 | 10/2001 | Van Dyke et al. |
| 2001/0032020 A1 | 10/2001 | Besselink |
| 2001/0047208 A1 | 11/2001 | Michelson |
| 2001/0051829 A1 | 12/2001 | Middleton |

| | | |
|---|---|---|
| 2002/0013600 A1 | 1/2002 | Scribner et al. |
| 2002/0022883 A1 | 2/2002 | Burg |
| 2002/0022888 A1 | 2/2002 | Serhan et al. |
| 2002/0026244 A1 | 2/2002 | Trieu |
| 2002/0029082 A1 | 3/2002 | Muhanna |
| 2002/0029083 A1 | 3/2002 | Zucherman et al. |
| 2002/0035400 A1 | 3/2002 | Bryan et al. |
| 2002/0045942 A1 | 4/2002 | Ham |
| 2002/0045944 A1 | 4/2002 | Muhanna et al. |
| 2002/0049498 A1 | 4/2002 | Yuksel et al. |
| 2002/0082608 A1 | 6/2002 | Reiley et al. |
| 2002/0082701 A1 | 6/2002 | Zdeblock et al. |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0107572 A1 | 8/2002 | Foley et al. |
| 2002/0107573 A1 | 8/2002 | Steinberg |
| 2002/0120269 A1 | 8/2002 | Lange |
| 2002/0120270 A1 | 8/2002 | Trieu et al. |
| 2002/0120334 A1 | 8/2002 | Crozet |
| 2002/0120336 A1 | 8/2002 | Santilli |
| 2002/0156528 A1 | 10/2002 | Gau |
| 2002/0165612 A1 | 11/2002 | Gerber et al. |
| 2003/0009226 A1 | 1/2003 | Graf |
| 2003/0023311 A1 | 1/2003 | Trieu |
| 2003/0028197 A1 | 2/2003 | Hanson et al. |
| 2003/0028251 A1 | 2/2003 | Mathews |
| 2003/0040799 A1 | 2/2003 | Boyd et al. |
| 2003/0045939 A1* | 3/2003 | Casutt ................. 623/17.15 |
| 2003/0055427 A1 | 3/2003 | Graf |
| 2003/0074076 A1 | 4/2003 | Ferree et al. |
| 2003/0100951 A1 | 5/2003 | Serhan et al. |
| 2003/0135276 A1 | 7/2003 | Eckman |
| 2003/0135277 A1 | 7/2003 | Bryan et al. |
| 2003/0135278 A1 | 7/2003 | Eckman |
| 2003/0176921 A1 | 9/2003 | Lawson |
| 2003/0204260 A1* | 10/2003 | Ferree ................. 623/17.11 |
| 2003/0204261 A1 | 10/2003 | Eisermann et al. |
| 2003/0220691 A1 | 11/2003 | Songer et al. |
| 2004/0024462 A1 | 2/2004 | Ferree et al. |
| 2004/0030391 A1* | 2/2004 | Ferree ................. 623/17.16 |
| 2004/0044410 A1 | 3/2004 | Ferree et al. |
| 2004/0082999 A1 | 4/2004 | Mathys, Jr. et al. |
| 2004/0093082 A1 | 5/2004 | Ferree |
| 2004/0102846 A1 | 5/2004 | Keller et al. |
| 2004/0117019 A1 | 6/2004 | Trieu et al. |
| 2004/0117022 A1 | 6/2004 | Marnay et al. |
| 2004/0133278 A1 | 7/2004 | Marino et al. |
| 2004/0153157 A1 | 8/2004 | Keller |
| 2005/0021042 A1 | 1/2005 | Marnay et al. |
| 2005/0021143 A1 | 1/2005 | Keller |
| 2005/0071011 A1 | 3/2005 | Ralph et al. |
| 2005/0085911 A1 | 4/2005 | Link |
| 2005/0085917 A1 | 4/2005 | Marnay et al. |
| 2005/0165485 A1 | 7/2005 | Trieu |
| 2005/0192671 A1 | 9/2005 | Bao et al. |
| 2005/0266581 A1 | 12/2005 | Droit et al. |
| 2006/0004453 A1 | 1/2006 | Bartish, Jr. et al. |
| 2006/0020342 A1 | 1/2006 | Ferree et al. |
| 2006/0041614 A1 | 2/2006 | Oe |
| 2006/0212122 A1 | 9/2006 | Perera |
| 2006/0235527 A1 | 10/2006 | Buettner-Janz et al. |
| 2006/0235528 A1 | 10/2006 | Buettner-Janz |
| 2006/0235531 A1 | 10/2006 | Buettner-Janz |
| 2007/0027547 A1 | 2/2007 | Rydell et al. |
| 2007/0100454 A1 | 5/2007 | Burgess et al. |

FOREIGN PATENT DOCUMENTS

| | | |
|---|---|---|
| CA | 2548780 | 12/2004 |
| DE | 9000094 | 1/1999 |
| DE | 29911422 | 8/1999 |
| DE | 10130825 | 3/2002 |
| EP | 0179695 | 4/1986 |
| EP | 0 346 129 A1 | 12/1989 |
| EP | 0 773 008 A1 | 5/1997 |
| EP | 0 919 209 A1 | 6/1999 |
| EP | 1 104 665 A1 | 6/2001 |
| FR | 2 372 622 | 6/1978 |
| FR | 2 732 841 | 4/1995 |
| FR | 2723841 | 3/1996 |
| FR | 2 787 014 | 6/2000 |
| FR | 2 797 179 | 2/2001 |
| FR | 2799116 | 4/2001 |
| FR | 2 805 985 | 9/2001 |
| FR | 2824261 | 11/2002 |
| JP | 63300758 A2 | 12/1988 |
| JP | 1308557 A2 | 12/1989 |
| JP | 01142293 | 4/1990 |
| JP | 2111358 | 4/1990 |
| JP | 2215461 A2 | 8/1990 |
| JP | 2224659 A2 | 9/1990 |
| JP | 2224660 A2 | 9/1990 |
| JP | 03275055 A | 5/1991 |
| JP | 03275056 A | 5/1991 |
| JP | 04303444 A | 10/1992 |
| JP | 05277141 A | 10/1993 |
| JP | 06-285099 | 10/1994 |
| JP | 08098850 A | 4/1996 |
| JP | 08098851 A2 | 4/1996 |
| JP | 11137585 A | 5/1999 |
| JP | 11009618 A | 10/1999 |
| WO | WO 90/11740 | 10/1990 |
| WO | 9105521 | 5/1991 |
| WO | WO 91/16867 | 11/1991 |
| WO | WO 93/16664 | 9/1993 |
| WO | WO 95/00082 | 5/1995 |
| WO | WO 96/01598 | 1/1996 |
| WO | WO 96/11642 | 4/1996 |
| WO | WO 96/27339 | 9/1996 |
| WO | WO 98/05274 | 2/1998 |
| WO | WO 98/55053 | 12/1998 |
| WO | WO 99/11203 | 3/1999 |
| WO | WO 99/22675 | 5/1999 |
| WO | WO 99/30651 | 6/1999 |
| WO | 0013619 | 3/2000 |
| WO | 0132100 | 5/2001 |
| WO | WO 01/15638 A1 | 8/2001 |
| WO | WO 01/68003 A1 | 9/2001 |
| WO | WO02/087480 | 11/2002 |
| WO | 2006016384 | 2/2006 |
| WO | 2006061114 | 6/2006 |

OTHER PUBLICATIONS

Artificial Disc Technology *Neurosurg. Focus*/vol. 9/Oct. 2000.

Bao, Q. et al, Artificial Disc Technology, Nerosurg. Focus, vol. 9, Oct. 2000, 7 pp.

Zdeblick, T. et al, Cervical Interbody Cages, An Animal Mode With and Without Bone Morphogenetic Protein, Spine, vol. 23, No. 7, 11 pp.

* cited by examiner

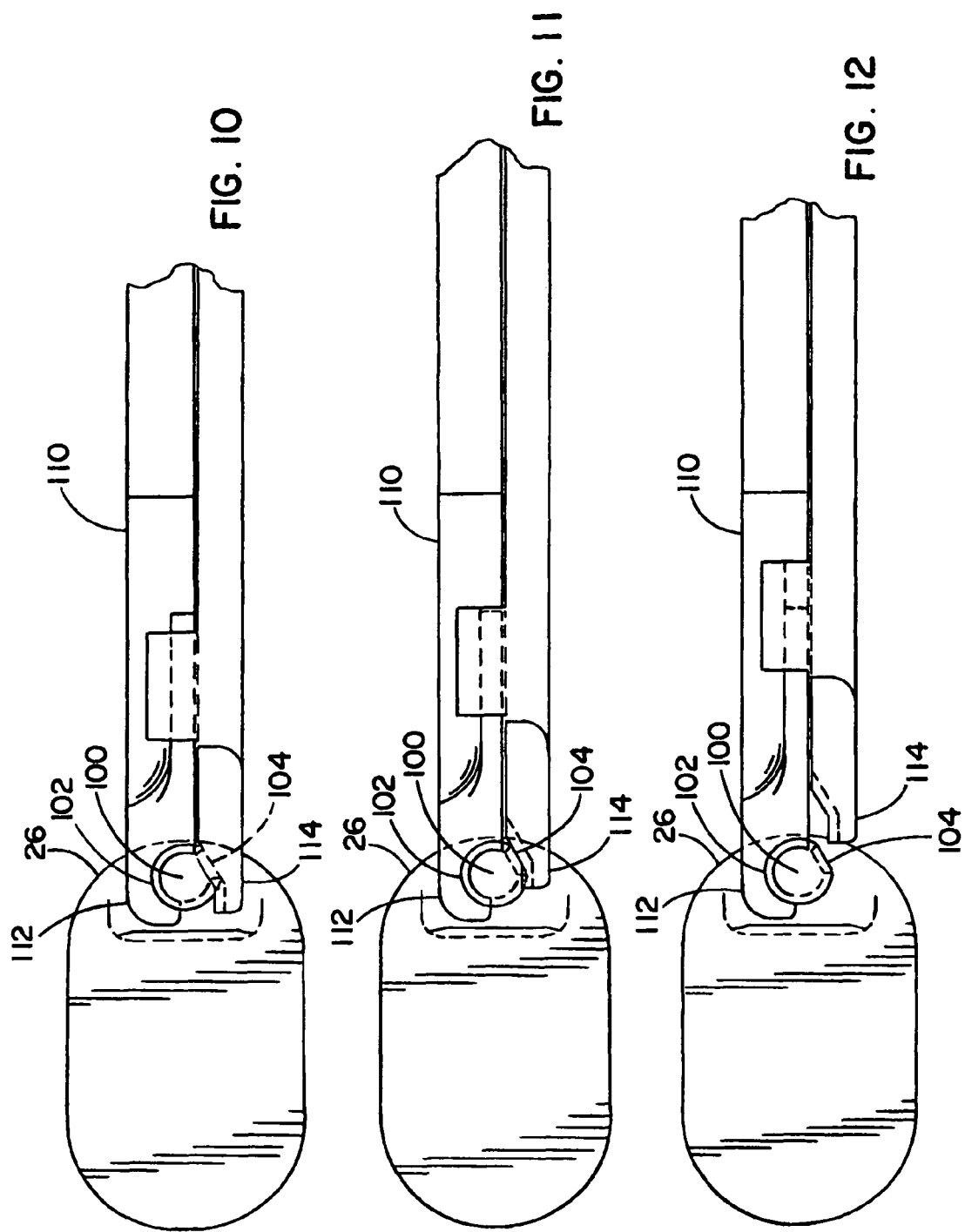

ARTIFICIAL DISC DEVICE

CROSS-REFERENCE TO RELATED APPLICATION

This is a continuation-in-part of prior application Ser. No. 10/282,620, filed Oct. 29, 2002 U.S. Pat. No. 7,001,433, and application No. 60/382,758, filed May 23, 2002 which is hereby incorporated herein by reference in its entirety. The entire disclosure of the prior application, from which a copy of the oath or declaration is supplied under paragraph 3 below, is considered as being part of the disclosure of the accompanying application, and is hereby incorporated by reference therein.

FIELD OF THE INVENTION

The invention relates to artificial intervertebral disc implants and, in particular, to a multiple piece disc implant that permits relative articulation and/or translation of the multiple pieces.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement results in, for instance, loss of mobility, urinary and fecal incontinence, and sciatica or pain experienced in the extremities.

Damage to or degeneration of the spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried and susceptible to damage disc. Because the nuclear material is flowable, extensive damage to the annulus is not necessary for leakage to occur.

Currently, approaches to treatment of spinal problems directly effecting the spinal cord are numerous. For instance, immobilization and high doses of corticosteroids may be employed. The dominant surgical procedures for treatment of these problems are spinal fusion and discectomy. Fusion is a method where adjacent vertebrae are immobilized so that they permanently secure to each other by having bone growth between and to the vertebrae, while discectomy involves removal of a portion or an entirety of a spinal disc.

However, the current practice of each of these procedures typically has certain limitations. With fusion, making a portion of the spine generally rigid produces a reduction in mobility, and drastically alters normal load distribution along the spinal column. Due to these factors, the non-fused portions of the spine experience stress and strain that are significantly increased over normal physiological motions. The increased stress and strain on the non-fused portions may lead to accelerated disc degeneration of the non-fused portions, particularly the adjacent levels of the spine.

Discectomy is effective for relieving sciatic pain by removing the damaged or herniated disc tissue compressing the spinal nerves. However, current discectomy often may lead to a reduction of the disc space between adjacent vertebrae, as well as instability in the affected portion of the spine. Such long-term effects with current discectomy often result in further surgery several years after the initial discectomy surgery.

A recent, though not new, development for spinal surgery of this type is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain. However, little success has been experienced with prosthetic disc implants due to the complexity of the natural disc structure and biomechanical properties of a natural spinal disc. As used herein, the term natural refers to normal tissue including portions of the spine and the disc.

Two types of prostheses for disc arthroplasty are currently believed to merit further development by medical science and research. One type is a total disc prosthesis, or TDP, where the entire spinal disc is replaced after radical discectomy. A typical TDP includes structures that together mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non-flowing prosthetic nucleus. Implantation of an DNP involves clearing of the natural nucleus from the annulus through the procedure known as nucleotomy, and inserting the DNP within the annulus. Accordingly, disc nuclear prostheses (DNPs) are typically smaller and require less extensive surgery than TDPs do.

In using disc implants, there are a number of issues with currently known TDPs and NDPs that attempt to mimic the biomechanical properties of a natural intervertebral disc. Some implants have been designed that provide shock absorption similar to a natural disc. However, these discs have typically been found incapable of maintaining structural integrity over the cyclic load life required of a disc that may be employed for 20 or more years. An early attempt at providing the polyaxial movement and rotation of the spine involved replacing the disc with a metal ball. Undesirably, loading between the ball and the end plates was highly concentrated such that bone subsidence caused the vertebrae to collapse around the ball.

Another issue is implant extrusion, defined as the tendencies for an implant not to remain seated, and for the implant to back out of its intended seat. To prevent this, many designs for disc implants attempt to secure to the end plates of the vertebrae by providing securement features on the implant. The securement features are usually a system of prongs or spikes or other physical protrusions designed to embed in the vertebrae. This, alone, violates the integrity of the end plates to a degree where revision surgery is limited, possibly to spinal fusion for immobilizing the spinal segment and fusing the vertebrae with posterior pedicle instrumentation. Violation of the vertebrae by the securement may cause bleeding, or calcification of the end plate, either of which can result in pain, loss of mobility, necrosis, or deterioration of any implant device. In mating the implant with the end plates, stress concentrations may result due to contour mismatch, such as with the above-described implant ball, which requires careful seating of the protrusions. To diminish these high stress points on the vertebrae, securement features will often be found on top and bottom plates that are fixed to cover the respective vertebra so forces are distributed thereacross.

Most implants are units that are implanted as a whole. Therefore, the adjacent vertebrae must be sufficiently distracted for the effective size of the implant including the top and bottom plates, which can be significantly increased when fastening protrusions are included. This requires greater invasiveness, which complicates surgery and leads to greater time for recovery and post-surgical pain. Furthermore, this often destroys any remaining utility for the annulus as a large incision must be made, in the event it is even retained. As the annulus does not heal well and suturing the annulus is difficult due to its tissue properties, the ability of the annulus to retain the implant is diminished if not eliminated, and implant extrusion often is not prevented by the annulus.

Most spinal disc procedures require an anterio-lateral approach to the surgical site. More specifically, spinal disc implants typically have a size roughly that of the natural spinal disc. In order to evacuate the disc space and implant the prosthetic device, space is required. Because of the geometry and structure of a vertebra, a natural disc, and an artificial disc implant, posterior surgical procedures do not typically permit the access required for evacuation of the disc space and implantation of the prosthetic device. Furthermore, an anterior-lateral approach to the surgical site, a general surgeon's service must be employed, typically in conjunction with an orthopedic surgeon or neurosurgeon, or both. Therefore, an implant device that may be implanted in multiple approaches is desirable.

Less extensive surgery is required for a DNP than for a TDP. A DNP replaces only part of the disc. Implantation of most DNPs with pre-formed dimensions requires a 5-6 mm, or larger, incision in the annulus for implantation. Some DNPs, such as those utilizing in situ curable polymers, may be performed percutaneously. In any event, implantation of a DNP requires minimal disc tissue resection, and can avoid violating the end plates of the vertebrae for securing. Moreover, recovery and post-surgical pain are minimal due to the minimal invasiveness of the procedure, and interbody fusion remains a viable revision surgery, It has been found herein that it is particularly important to restore the normal range of motion of the spine. Specifically, it has been found to be more important to provide flexion/extension, lateral bending, and axial rotation of the spine, than it is to provide the compressive modulus of elasticity. More particularly, it is believed that failure to provide the normal range of motion has the deleterious effects, as discussed above, of spinal fusion. In contrast, it is believed that the loss of compressive elasticity in that region may be borne by the other natural spinal discs. As the implant needs to restore or maintain disc height, it should withstand a significant amount of compressive load in the proper physiological manner so end plate damage is not induced that may lead to pain and implant subsidence.

A number of attempts have been made at artificial discs, each presenting deficiencies. Some procedures and devices rely on lateral or anterior surgical procedures, which are highly invasive and traumatic and which carry high surgical risk.

Accordingly, there has been a need for an improved disc implant for mimicking the biomechanical properties of a natural disc.

SUMMARY OF THE INVENTION

In accordance with one aspect of the present invention, a multi-piece nucleus implant device is disclosed for replacing a nucleus removed by a nucleotomy. The implant may include at least a first shell or plate member, a second shell or plate member, and a bearing member providing at least one direction of movement between the two shells, and preferably being a polyaxial articulating bearing member. The articulating bearing member provides for the natural movement of the spine including flexion/extension, lateral bending, and rotation. Each of the plate members and the articulating bearing member are generally formed to be rigid. Therefore, the implant is capable of supporting the compressive and cyclic loads required of a natural disc.

In some forms, the implant may also provide for relative sliding and/or translation between the shells and the articulating bearing member. Specifically, the surfaces between the shells and the articulating bearing member are able to slide relative to each other. As the mechanics of a natural disc are those of a viscous fluid, the bend of the spine in one direction forces the fluid in an opposite direction. The shells of the implant rotate relatively in a particular manner due to bending forces on the implant. However, due to the dimension requirements of the implant, the shells need not rotate around a fixed pivot point. To mimic the behavior of the natural nucleus in this manner, and to do so with rigid members, the articulating bearing member permits the components of the implant to shift relative to each other. Furthermore, some forms of the implant allow a center insert or spacer member that may shift away or by sliding and/or translating from the direction of bending to more closely mimic the behavior of a natural disc, as will be discussed below.

One aspect of the present invention is providing a polyaxial articulating device utilizing a concave recess and a dome member formed between the shells. The dome member and recess form an articulating bearing member permitting polyaxial movement of the shells relative to each other, and the dome surface and recess may slide or translate relative to each other.

In some forms, the stiffness of the polyaxial rotation of the articulating bearing member may be controlled and varied. The respective radii of curvature for, and hence the fit between, the recess and dome surface may be varied to produce a different stiffness. In general, if the radius of curvature of the recess is greater than that of the dome surface, there is a less restricted condition, and the stiffness is lowered. Conversely, if the radius of curvature of the recess is lower than that of the dome surface, there is a more restricted condition, and the stiffness is increased.

As another aspect of the present invention, the outer surfaces of the implant that contact the end plates of adjacent vertebrae may be provided with a convexity selected according to the natural, overall concavity of the end plate. When the convexity of the outer surfaces of the implant match the concavity of the end plate, forces will be generally evenly distributed across the end plate and high stress points are avoided. The construction of the implant, then, avoids bone subsidence issues and the integrity of the end plates is maintained. If revision surgery is necessary, this permits the surgery to employ a range of desired methods.

Alternatively, the convexity of the outer surfaces of the implant may be slightly decreased. The bone of the end plate is slightly elastically deformable. A slight mismatch between the outer surfaces and the end plate allows residual stresses to develop between the outer periphery of the outer surface shell and the end plate, stresses which serve to hold the generally convex outer surface of the implant in proper position. Any such alteration should be restricted to the degree that bone subsidence does not occur.

In another aspect of the present invention, the implant has a generally oval or racetrack shape. A natural disc and nucleus are kidney-shaped, having a smaller dimension in the anterior-posterior direction than in the lateral direction. Therefore, the space provided by the removal of the nucleus has a similar shape. Though the kidney-shape may or may not be replicated, implant performance has been found herein to benefit from having a wider lateral dimension than anterior-posterior dimension, such as a generally oval, racetrack, or trapezoidal shape, for the shells. To further reduce the size of the incision made in the annulus, which improves the ability of the annulus to prevent implant extrusion, the shells of the implant may be inserted with a lateral end leading first through a posterior incision in the annulus. In this manner, the shells may then be pivotally rotated within the nuclear space.

To facilitate the rotation of the shells within the nuclear space, an embodiment of the invention includes a post for gripping, inserting, and rotating one or more of the shells. The post may have a flat portion and a round portion so that a tool may grip the post in a first position such that the post may not rotate relative to the tool during insertion. Once inserted, the tool may partially release the post so that the tool no longer abuts the flat, and the post may rotate relative to the tool without being fully released. The tool may then direct the rotation of the shell within the nuclear space.

It has been found that distraction of the annulus helps alleviate pain and improves stability of the intervertebral joint. As discussed above, the shells of the implant do not necessarily replicate the shape of the natural nucleus. In the event the shape of the implant may not match that of the natural nucleus, the outer periphery of the implant may engage and stretch portions of the annulus, thereby providing tension to those portions of the annulus. In addition, an outer curtain or sheath in the form of, for instance, a pleated bellows may be provided spanning between and generally sealing the compartment between the shells. The bellows may then be injected with a material, such as gas or liquid, such that the bellows or curtain distends to apply pressure on the interior of the annulus. Additionally, the injected material may expand slightly in situ the nucleus implant. As a further benefit, the bellows prevents foreign material from entering the implant device which otherwise may hinder or deteriorate the performance of the implant, particularly the articulating bearing member.

In a further aspect of the present invention, it is desirable to restrict the anterior-posterior bending of the implant. Generally, the greatest deflection between vertebrae is approximately 15°. Due to the polyaxial nature of the movement provided by the implants of the present invention, the lateral direction provides approximately 15°, and the anterior-posterior directions may permit greater motion. In some embodiments, then, it is desirable to mechanically prevent deflection beyond 15°. In one form, the shells include a short wall extending towards the opposing shells that physically abut when the 15° bend is reached. In another form, a spacer member may be an annular ring extending from its periphery and between the shells such that the shells contact the ring when the 15° angle is reached. In another form, the shells may be provided secured together by a cable that connects the shells to prevents the shells from bending beyond 15° and to prevent the spacer member from escaping from between the shells.

In some embodiments, each shell may provide for rotational, sliding, or translational movement, and an insert or spacer member may be located between the two shells and may have two surfaces moving against the respective shells. It is believed multiple wear surfaces interfacing increases the life expectancy of the implant with respect to wear. In some forms, each shell may have a concave recess, and the spacer has two dome surface portions, each facing a respective shell, and forms an articulating bearing member with each concave recess. In other forms, the spacer member may have a dome surface on one side meeting a concave recess in a shell thereby providing for polyaxial rotation, translation, and sliding, and may have a flat on another side engaging a flat surface in a recess in a shell thereby providing for linear translation and planar rotation.

In some forms of the multi-piece implant, a multi-piece implant is disclosed where the pieces may be sequentially inserted through an incision in the annulus for assembly within the disc nucleus space. As such, the incision need not provide space for the entire implant to be inserted, and the invasiveness of the procedure is minimized, which in turn diminishes post-surgical recovery and pain. In addition, any distraction of the adjacent vertebrae that need occur is minimized by inserting the implant in portions. As the incision does not allow the entire implant to be inserted, the remaining integrity of the annulus may be utilized. Specifically, the annulus may be used to retain the implant in place within the annulus and in the nucleus space. Therefore, protrusions for securing the implant to end plates of adjacent vertebrae are unnecessary to prevent the implant from escaping from between the vertebrae.

In a similar form of the multi-piece implant, each shell may include a concave recess and a double-domed spacer member. By providing a dome surface for each of the recesses, the wear upon the surfaces therebetween is reduced, as described. The pieces are sequentially inserted in any order through the incision of the annulus, though it is preferred that the shells are inserted first to prevent injury to the end plates. The shells may include aligned ramps, or a similar structures, to the side of their respective concave recesses to allow the spacer member to be inserted therebetween. In addition, the members may be inserted, and then one or more may be rotated or translated so that the spacer member is prevented from backing out through the incision in the annulus and/or to further expand the implant. This embodiment then provides for polyaxial movement and allows the shells each to slide and/or translate relative to the spacer member, and the spacer member may slide or translate away from the direction of bending. It should be noted that the maximum clearance provided by the incision in the annulus need be that required by the largest of the three pieces.

A further form of the multi-piece implant includes a shell with a concave recess, as described above, a shell with steps or ramps rising towards its center, and a spacer member having one side stepped or ramped and the other side domed. Here, the shells may be inserted through the incision in the annulus so that the stepped portion of the shell is facing the incision. The spacer member may be then forced between the shells such that the stepped spacer member cams up the steps of the stepped shell until the dome surface is received in the concave recess of the other shell. The stepped portion of the shell may include sidewalls to direct generally the path of the stepped spacer member. The sidewalls may be positioned so that the spacer member may slide or translate a short distance along the steps, while also preventing overtranslation. Preferably, the steps of the shell extend from a lateral side of the shell. In one form, the stepped shell is rotated after expansion, while in another the stepped shell may be rotated and then the implant is expanded.

In a further aspect of the invention, a multi-piece implant device is disclosed where the entire implant is inserted through an incision in the annulus. The implant is inserted in a compressed or collapsed state as a unit and then expanded after implantation. The size of the incision in the annulus need only provide for the size of the unexpanded implant. As discussed, the implant may be inserted with an end having a shorter, lateral dimension leading first and then may be rotated once the trailing portion of the implant is inserted in the incision. Alternatively, rotation can begin before the implant is entirely inserted through the incision so that rotation occurs as the implant is being pushed through the incision. Accordingly, the incision need only provide for insertion of the compressed implant, the invasiveness of the procedure is minimized, the post-surgical recovery and pain are minimized, distraction of the adjacent vertebrae is minimized, the annulus will assist in retaining the implant in place, and protrusions for securing the implant are unnecessary.

In an embodiment of this aspect, an implant with a helically stepped spacer member that may be inserted in a collapsed state and then expanded is provided. The stepped spacer member allows the implant to be expanded step by step to the desired vertical height. At least one shell has a concave recess into which a dome surface of a spacer member is received. The spacer member has two opposing parts, one of which may be integral with a second shell or may have a dome surface received into a concave recess in the second shell. The opposing spacer member parts have helically oriented steps, and the spacer member and/or implant may be inserted or assembled within the nucleus space in a compressed or collapsed state or arrangement. Once implanted, the opposing parts of the spacer member may be rotated relative to each other such that the steps ratchet up, thereby expanding the spacer member to an expanded arrangement. Each dome surface and recess provide for polyaxial movement of the implant, translation, and arcuate sliding, as described above.

In a further embodiment, a spacer member may be provided with a member rotating around a longitudinal axis and connected to one or more non-rotating wedges. The rotating member is turned to pull or push any wedges from a first, compressed position to a second, expanded arrangement. The wedges are forced between two portions of the spacer member to expand the spacer member and, therefore, to expand the implant. At least a portion of the spacer member has a dome surface that is received in a concave recess of a shell.

In another embodiment, the spacer member may include cam surfaces which cam against mating cam surfaces of another portion of the spacer member or of one of the shells. The cam surfaces may rotate relative to each other, thus camming the portions to expand, thereby expanding the implant. Again, at least a portion of the spacer member has a dome surface that is received in a concave recess of a shell.

In an additional aspect of the present invention, the spacer member may form an internal cavity or cannister. In one embodiment, the cavity may be formed by the spacer member and a portion integral with one shell such that the spacer member and shell expand relative to each other, thereby expanding the implant. In another embodiment, the cavity may be formed by two portions of the spacer member that expand relative to each other, thereby expanding the implant. In a further embodiment, the cavity may be formed by two end pieces and a cylindrical wall of the spacer member such that the end pieces expand along the cylindrical wall to expand the implant. In any of these embodiments, the spacer member may include an internal balloon for receiving an injected material so that the injected material is captured within the cavity. Alternatively, injected material may be forced into the cavity such that the portions of the cavity are sealed. Curable material may be used such that the expanded spacer member is rigid. Alternatively, the spacer member may be filled with an elastomeric or flowable material that provides some shock absorption.

Various forms of the present invention may be implanted in an anterior, anterior-lateral, or a posterior surgical procedure. The size of each implant component or a collapsed implant may be such that each may be inserted with only a small incision in the annulus. Furthermore, the spinal structure permits the components or collapsed implant to be inserted through the posterior of the spine. A posterior approach to the surgical site reduces the invasiveness of the procedure, and may often be performed by a single orthopedic surgeon or neurosurgeon without a need for a general surgeon, and thus substantially decreases the cost and complexity of the procedure.

BRIEF DESCRIPTION OF THE DRAWINGS

In the drawings.

FIG. 10 is a top plan view of a shell and an insertion implement in a locked position;

FIG. 11 is a top plan view of the shell and the insertion implement of FIG. 10 in an intermediate position;

FIG. 12 is a top plan view of the shell and the insertion implement of FIG. 10 in an unlocked position;

DETAILED DESCRIPTION OF THE PREFERRED EMBODIMENTS

Figure 1:
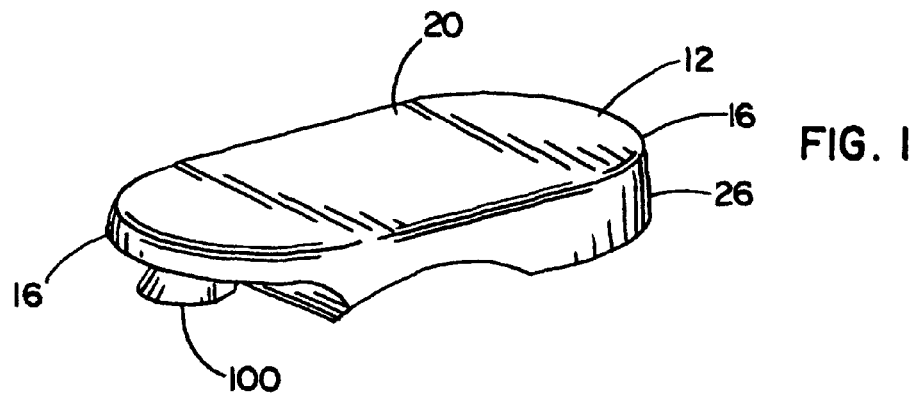
FIG. 1 is a first perspective view of a shell of an implant of an embodiment of the present invention.
Figure 2:
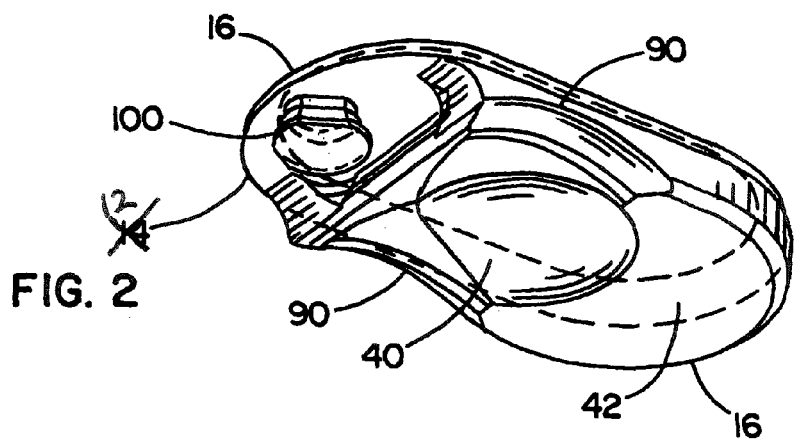
FIG. 2 is a second perspective view of the shell of FIG. 1.
Figure 3:
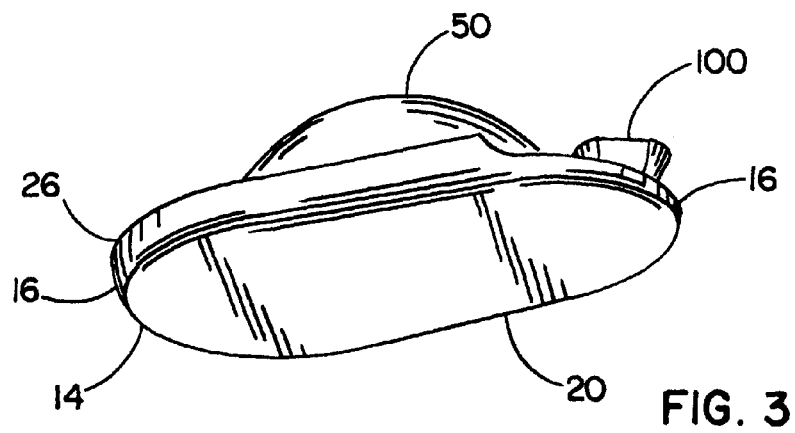
FIG. 3 is a first perspective view of a shell including a dome surface.
Figure 4:
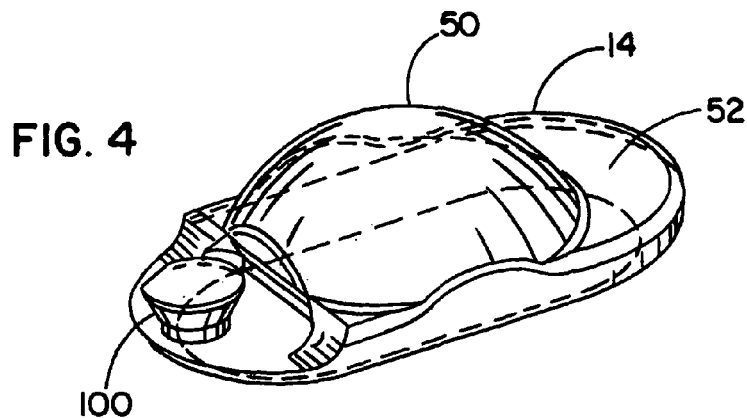
FIG. 4 is a second perspective view of the shell of FIG. 3.
Figure 5:
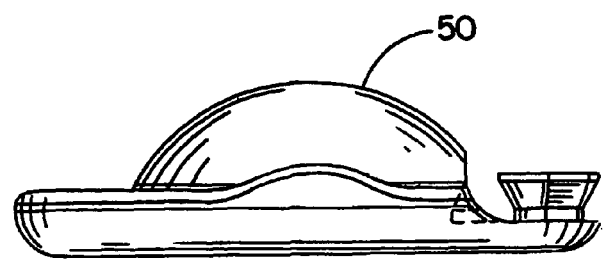
FIG. 5 is a side elevational view of the shell of FIG. 3.

Referring now to the FIGURES, an implant device 10 is depicted including a top shell 12 and a bottom shell 14. As used herein, the terms top shell and bottom shell are simply referential for the arrangement of the shells as depicted, and the arrangement could be reversed. The implant 10 is a prosthetic nucleus implant for replacing the nucleus of a damaged natural spinal disc. The nucleus of the natural spinal disc is generally cleared by a procedure known as a nucleotomoy where an incision is made in an annulus surrounding the nucleus, whereupon the nucleus is substantially removed. Typically, a small amount of the viscous nuclear material remains in the disc space, and this material can be used to provide an interface for reducing possible stress points due to incongruities between the implant 10 and end plates of the adjacent vertebrae.

The implant 10 is inserted through the incision in the annulus such that the annulus remains attached to adjacent vertebra and holds the implant 10 in an intervertebral position in the nucleus space. In order to utilize the annulus in this manner, the implant 10 may be inserted either in components or pieces, or may be inserted in a compressed or unexpanded state or arrangement. Once in situ or implanted, the implant 10 may be assembled, expanded, or both, as will be described below. Accordingly, the incision in the annulus is smaller than a typical nuclear implant requires, and the surgery is minimally invasive. Because the size or arrangement of the implant 10 is altered after being inserted through the annulus, the expanded or assembled implant 10 cannot escape from the annulus. By using the annulus to prevent implant extrusion or escape, protrusions or other securements that penetrate, abrade, or otherwise disturb the integrity of the surface of the end plates are eliminated. By retaining the annulus, the vertebral sections have greater stability and may more closely return to normal motion, as well as the site minimizes scarring from removing or otherwise excessively damaging the annulus.

Each shell 12, 14 has an outer surface 20 for engaging and mating with an adjacent vertebra (not shown), specifically with an end plate of a vertebra. The outer surface 20 of each shell 12, 14 is preferably smooth to avoid disturbing the surface of the end plates. The end plates of the adjacent vertebrae have naturally occurring concave surfaces mating with the outer surfaces 20 of the shells 12, 14. The vertebra above the implant 10 has a slightly different concavity from that of the vertebra below the implant 10. Preferably, the outer surface 20 of each shell 12, 14 is contoured with a convexity 18 (see, e.g., FIGS. 26, 33, 34) corresponding to the concavity of its respective adjacent vertebra. In one embodiment, the radius of curvature of the convexity 18 of the outer surface 20 of each shell 12, 14 matches the radius of curvature of the concavity of the adjacent vertebra. In another embodiment, the radius of curvature of the convexity 18 of the outer surface 20 of each shell 12, 14 is slightly less than the radius of curvature of the concavity of the adjacent vertebra. As the bone of the end plate is slightly elastically deformable, the slight mismatch of the interface between the outer surface 20 of the shell 12, 14 and the respective vertebrae impart a slight residual stress that serves to impede movement of the shells 12, 14 relative to the vertebrae. As a further alternative, the radius of curvature of the convexity 18 of the outer surface 20 of each shell 12, 14 may be slightly greater than the radius of curvature of the concavity of the adjacent vertebra. Again, as the bone is slightly elastically deformable, the slight over-convexity of the outer surfaces helps insure a more even distribution of compressive force on the implant and adjacent vertebra. Any such mismatch should not be such that bone subsidence, as described above, occurs.

Preferably, each shell 12, 14 has a peripheral shape 26 of an oval or a racetrack shape to have a greater lateral dimension D1 than longitudinal or anterior-posterior dimension D2. Alternatively, each shell 12, 14 may have a trapezoidal, round, or kidney shape (see, e.g., FIGS. 31-32). In addition, the peripheral shape 26 may be rounded or radiused. In order to most evenly distribute the compressive forces experienced by the implant 10 across the end plate, the size and shape 26 of the shells 12, 14 preferably cover as much of the end plate as possible. In addition, the periphery 26 of the shells 12, 14 preferably contacts and places in tension at least a portion of the inner surface of the annulus in which they are implanted, as will be discussed below.

Figure 7:
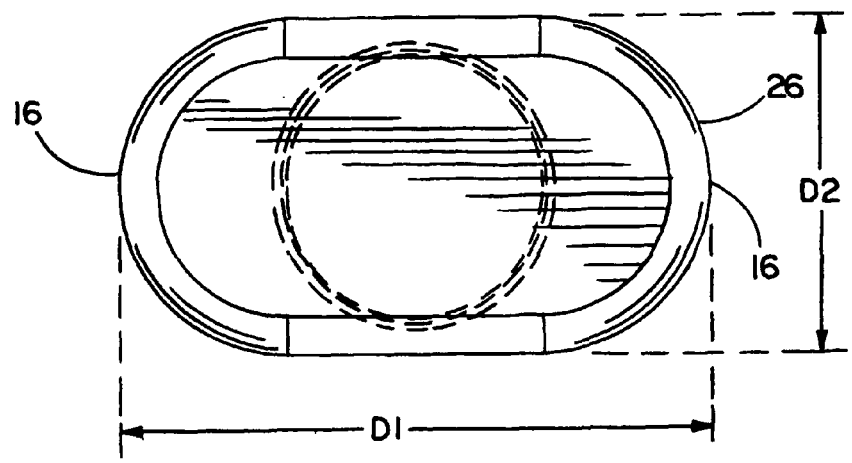
FIG. 7 is a top plan view of an implant with a spacer member in phantom
Figure 6:
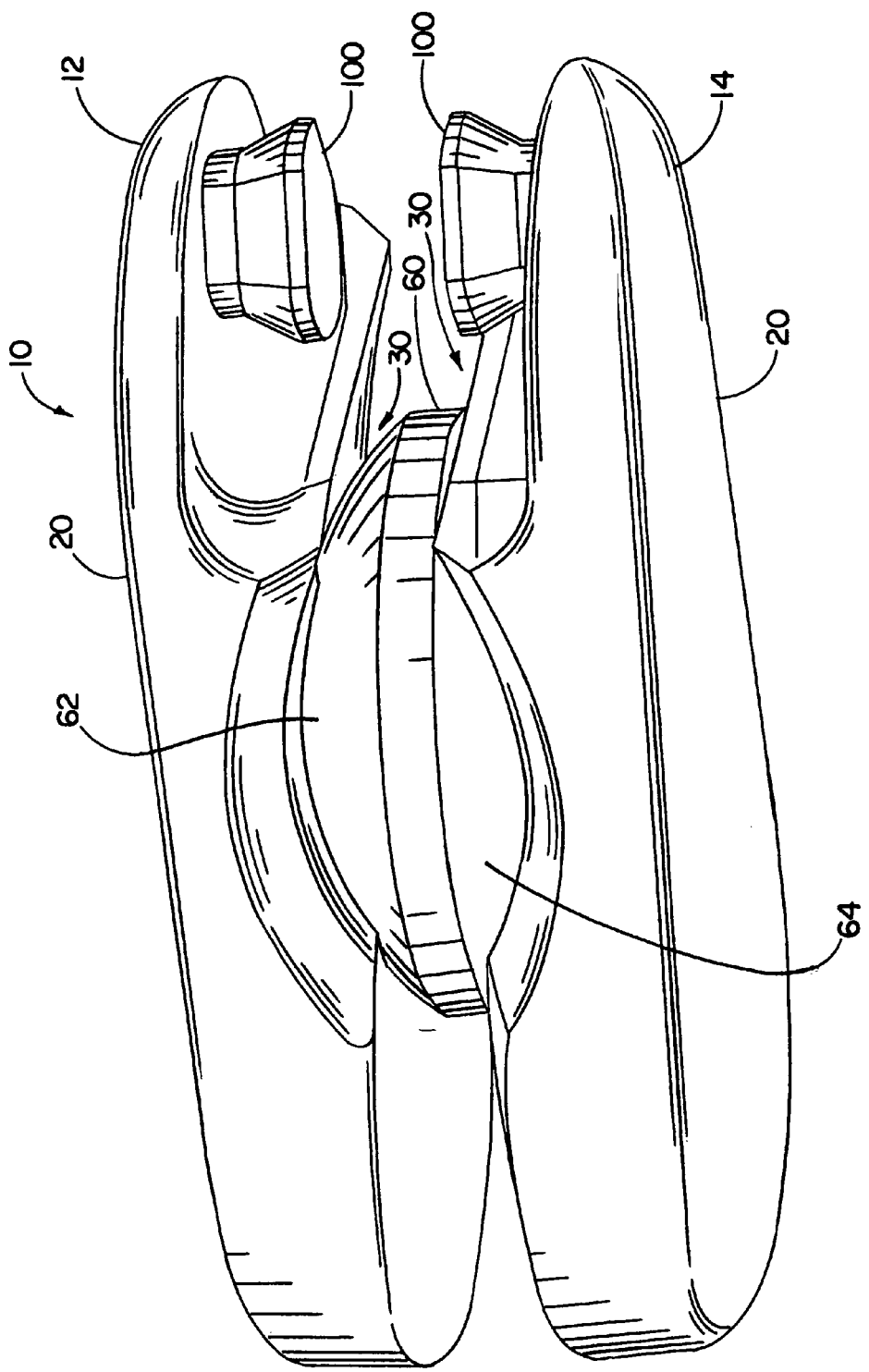
FIG. 6 is a perspective view of an implant of an embodiment of the present invention.
Figure 8:
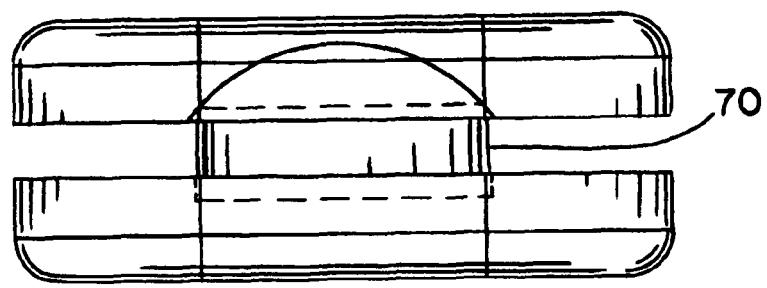
FIG. 8 is a side elevational view of the implant of FIG. 7.
Figure 9:
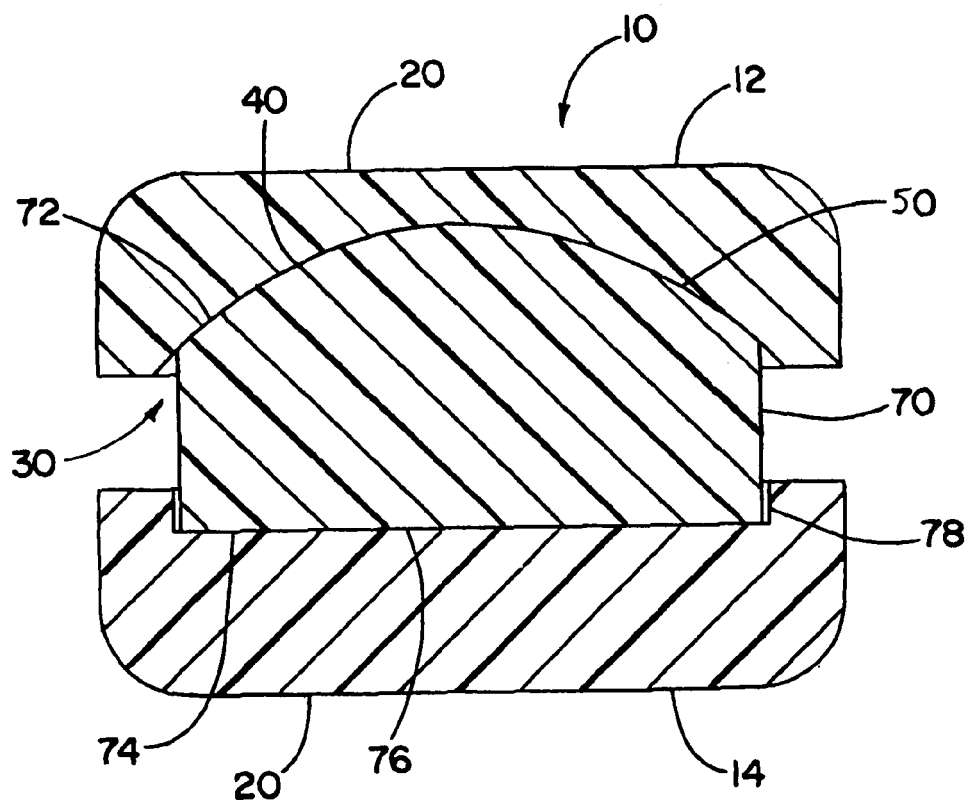
FIG. 9 is a cross-sectional view of the implant of FIG. 7.
Figure 13:
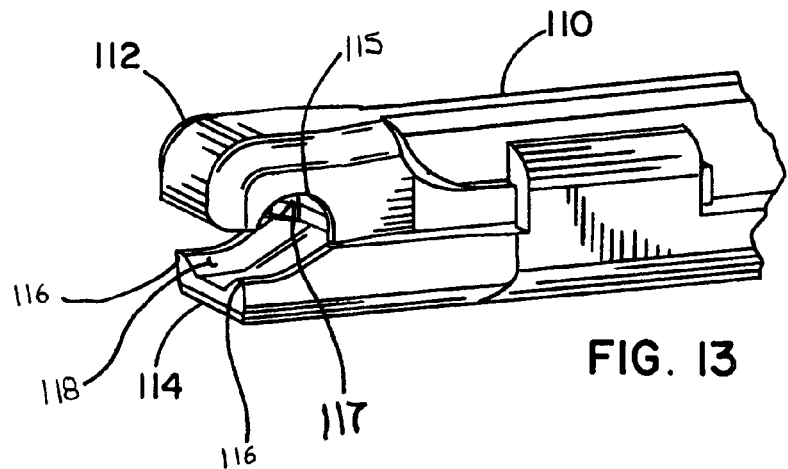
FIG. 13 is a perspective view of the insertion implement of FIG. 10.

Each implant 10 is provided with at least one polyaxial articulating bearing member 30 formed between a concave recess 40 formed in the top shell 12 and a dome surface 50. The dome surface 50 and the surface of recess 40 mating with the dome surface 50, as well as another sliding surfaces as described herein, are preferably smooth for low friction engagement. As depicted in FIGS. 1-5, the recess 40 is formed in a face 42 (FIG. 2) that opposes the bottom shell 14, and the dome surface 50 is formed on a face 52 (FIG. 4) of the bottom shell 14 that opposes the top shell 12. Alternatively, as depicted in FIG. 6, an implant 10 may be provided with a pair of polyaxial articulating bearing members 30, where a spacer member or insert 60 is provided with opposite faces 62, 64 each including a dome surface 50 for being received in a concave recess 40 in each of the confronting shells 12, 14. As a further alternative, FIGS. 7-9 depict a spacer member 70 having opposite faces 72, 74, where the face 72 includes a dome surface 50 and the face 74 includes a flat 76. For the spacer member 70, the dome surface 50 is received in a recess 40, and the flat 76 is received in a similarly shaped, though slightly larger, recess 78 with a flat surface in the bottom shell 14 such that the flat 76 may slide or translate in the recess 78. Two wear surfaces reduce the overall wear experienced in comparison to a single wear surface, and as such two such surfaces are preferred. It should be noted that the radius of curvature of opposing sides of a spacer 60 providing two wear surfaces need not be identical.

Each articulating bearing member 30 between a dome surface 50 and a recess 40 provides polyaxial motion of the concave recess 40 relative to the dome surface 50. Particularly, the bearing member 30 permits flexion/extension, lateral bending, and rotational movement of the recess 40 relative to the dome surface 50. In addition, mating surfaces between the spacer member 60 and the shells 12, 14 each provide for relative sliding or translation, as will be discussed below. The stiffness of the articulating bearing member 30 may be varied or controlled. Specifically, the concave recess 40 and the dome surface 50 each have respective radii of curvature. When the radius of curvature of the recess 40 is greater than the radius of curvature of the dome surface 50, the stiffness is decreased. When the radius of curvature of the recess 40 is smaller than the radius of curvature of the dome surface 50, the stiffness is increased.

In order to more closely mimic the behavior of a natural disc nucleus, the shells 12, 14 and any spacer member, such as but not limited to the spacer members 60, 70, may slide or translate relative to each other. The recess 40 and dome surface 50 may pivot or rotate relative to each other, as well as slide along their mating surfaces. For the flat 76 and flat surface in the recess 78, for instance, the sliding is translational. A natural disc includes a nucleus of viscous fluid, and the fluid moves away from the direction of bending or compression of the nucleus. The shells 12, 14 of the implant 10 are moved in a manner that follows the movement of the vertebrae. However, the spacer member 60 cannot enlarge in the opposite direction of the bending and compress in the direction of bending, as the natural disc can. By allowing the spacer member 60 to slide or translate relative to the shells 12, 14, the spacer member 60 may shift away from the direction of bending, thereby more accurately mimicking the compression of a natural nucleus. In addition, due to the small height of the implant 12, the pivot point of the top shell 12 relative to the bottom shell 14 is below the bottom shell 14. Accordingly, the recess 40 of the top shell 12 preferably may shift across the dome surface 50 such that the pivot point moves along with the top shell 12.

Similarly, for any vertebra-disc-vertebra segment, the center of rotation changes slightly during flexion/extension motion. To provide for this, the radius of curvature of the recess 40 may be larger than the radius of curvature of the dome surface 50 in the anterior-posterior direction. Therefore, the dome surface 50 may slide relative to the recess 40 in a manner that allows the shifting of the center of rotation.

As described above, the implant 10 may be inserted in pieces, specifically inserted sequentially or serially. As shown in FIGS. 1-5, the implant 10 has two principal pieces, namely the top shell 12 and bottom shell 14 where the top shell 12 has the concave recess 40 for receiving the dome surface 50 of the bottom shell 14. As shown in FIG. 6, the implant 10 has three principal pieces, namely the top and bottom shells 12, 14, and the spacer member 60 where the shells 12, 14 have concave recesses 40 for receiving the dome surfaces 50 of the opposite faces 62, 64 of the spacer member 60. In each of these FIGS. 1-6, at least one of the shells 12, 14 includes a ramp 90 adjacent to each recess 40. The ramp 90 may have an arcuately shaped profile against which the dome surface 50 may cam. Regardless of the order in which the shells 12, 14, or spacer member 60 are inserted through the incision in the annulus, the ramps 90 allow the pieces to be forced together by pushing any dome surface 50 against and over an aligned ramp 90 in a camming action during insertion such that the dome surface 50 cams against the aligned ramp 90. In this manner, the size of the incision made in the annulus may be minimized, as it need only provide for the largest piece to be inserted, and the annulus may be utilized for retaining the implant 10 in the nucleus space.

To further minimize the size of the incision made in the annulus, the shells 12, 14 having a smaller anterior-posterior dimension D2 than lateral dimension D1 may be inserted with a shorter, lateral end 16 leading first through a posterior incision in the annulus. The maximum clearance necessarily provided by the incision in the annulus need only be that required by the largest of the three pieces. In other words, the incision forms a deformable hole or bounded loop, and each component or piece of the implant 10 has a minimal encirclement required that the incision must permit to pass therethrough. Part of the instrumentation may include a device for cutting a precision incision into the annulus that is just large enough to insert the implant. The incision need only be large enough for the largest of the minimal encirclements of the individual pieces. Once implanted, the shells 12, 14 and/or any spacer such as spacer member 60 may be rotated within the nuclear space so that the short dimension D2 is no longer aligned with the incision in the annulus.

The shells 12, 14, and the implant 10 in general, may be rotated by an insertion tool 110 either during insertion or after assembly within the nuclear space (see FIGS. 1-6, and 10-13). The shells 12, 14, may include a post 100 including a generally circular outer surface 102 and at least one flat 104 formed on the outer surface 102. As depicted in FIGS. 10-13, the tool has several positions and has an upper, stationary jaw 112 and a lower jaw 114 which may reciprocate along the longitudinal axis of the tool 110. Referring to FIG. 10, the lower jaw 114 of the tool 110 abuts or confronts the flat 104 so that the post 100 is secured in the jaws 112, 114 so that the tool 110 and post 100 are in a locked position for insertion of the shell 12, 14. As can be seen in FIG. 11, the lower jaw 114 is in an intermediate position so that the lower jaw 114 is drawn a short distance away from the post 100 so that the lower jaw 114 does not abut or confront the flat 104. In the intermediate position, the post 100 remains captured in the jaws 112, 114. However, the post 100 may rotate relatively within the jaws 112, 114 so that the shell 12, 14 may be rotated during or after insertion in the annulus. FIG. 12 further shows a released position wherein the lower jaw 114 is drawn away from the post 100 so that the tool 110 may be removed from the post 100 and the tool 110 may be extracted from the implantation site. As can be seen, the post 100 enlarges in a direction away from the shell 12, 14 to which it is attached. The jaws 112, 114 each have opposed walls 115, 116, respectively. The walls 115, 116 are shaped as to follow the contour of the jaws 112, 114 while providing recesses 117, 118 between the walls 115, 116. Thus, the jaws 112, 114 may simultaneously encircle and manipulate a pair of posts 100 on a pair of shells 12, 14 in the manner described. The recess 118 between the walls 116 of the jaw 114 has an open terminal end 119 such that the lower jaw 114 may pass along an edge of the post 100 in a line so as to reciprocate between the locked, intermediate, or unlocked positions.

Figure 14:
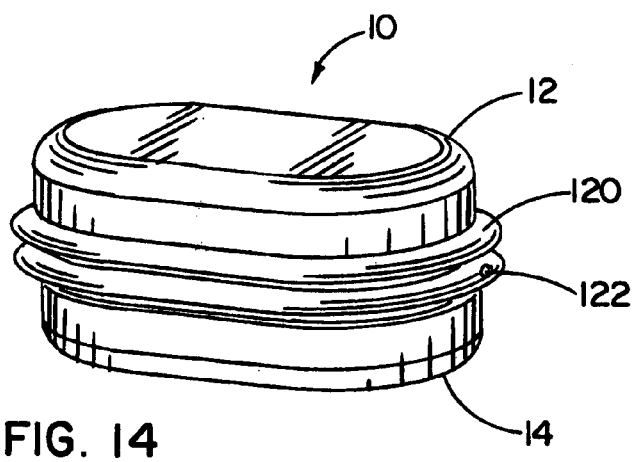
FIG. 14 is a perspective view of an implant including a curtain.
Figure 15:
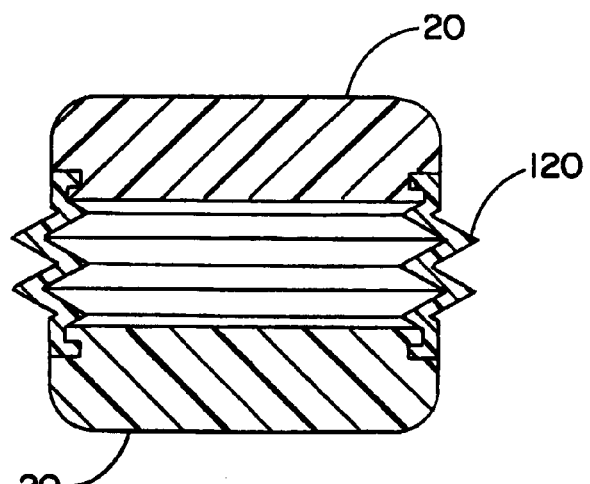
FIG. 15 is a side elevation cross-sectional view of the implant of FIG. 14.

As discussed above, the shells 12, 14 of the implant 10 do not necessarily replicate the shape of the natural nucleus so that the periphery 26 of the implant 10 may abut and stretch portions of the annulus, thereby providing tension to those portions of the annulus. It has been found that tension on the annulus alleviates pain and improves stability of the intervertebral joint. As depicted in FIGS. 14-15, an outer curtain in the form of, for instance, a pleated bellows 120 is secured to the shells 12, 14. The bellows 120 may form a seal between the shells 12, 14 and extend thereabout so that the implant 10 may be injected with a material. The material may be gas or liquid or other flowable material, such that the bellows 120 distends to apply pressure on the interior of the annulus. Preferably, the bellows is filled with saline or other non-curable material. Additionally, the injected material may slightly expand the implant 10 to provide some shock absorption and additional distraction if so desired. Furthermore, the bellows 120 prevents foreign material from entering the implant 10 which otherwise may hinder or deteriorate the performance of an articulating bearing member 30. In some embodiments, the material may be hydrogel pellets and the bellows 120 may include a permeable or semi-permeable portion to allow fluid absorption. By using pellets, the material may move within the implant 10 as any bearing member 30 articulates between the shells 12, 14. By inflating or expanding the bellows 120, or a similar structure, pressure is applied radially to the annulus to place the annulus in tension.

The bellows 120 may be attached to the shells 12, 14 by several methods. For instance, heat bonding, adhesive bonding, or a compression seal may be used to make the bellows firmly and permanently bonded to the shells 12, 14. Preferably, the compliance of the bellows 120 is less in the posterior direction than in anterior and lateral directions. As used herein, the term compliance refers the ability for a material to stretch. The bellows 120 may be provided with a portal 122 to which a catheter or needle can be attached for injecting the bellows 120, and the portal 122 includes a sealing mechanism.

Figure 16:
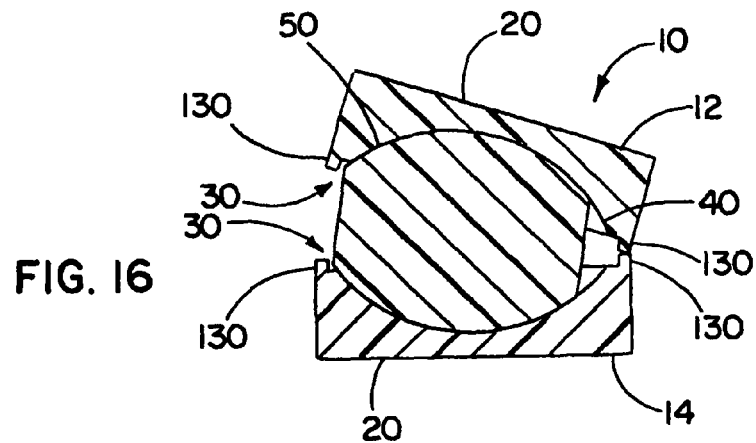
FIG. 16 is a cross-sectional view of an implant with walls to restrict motion of the shells in the anterior-posterior or lateral directions and to prevent the spacer from escaping.
Figure 17:
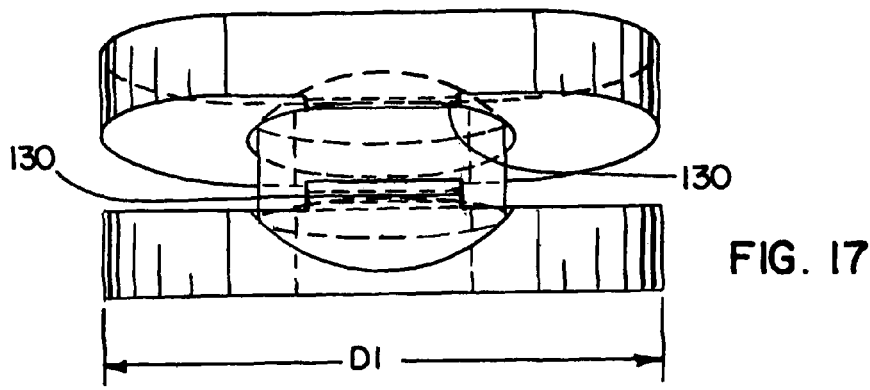
FIG. 17 is a perspective view of the implant of FIG. 17.
Figure 18:
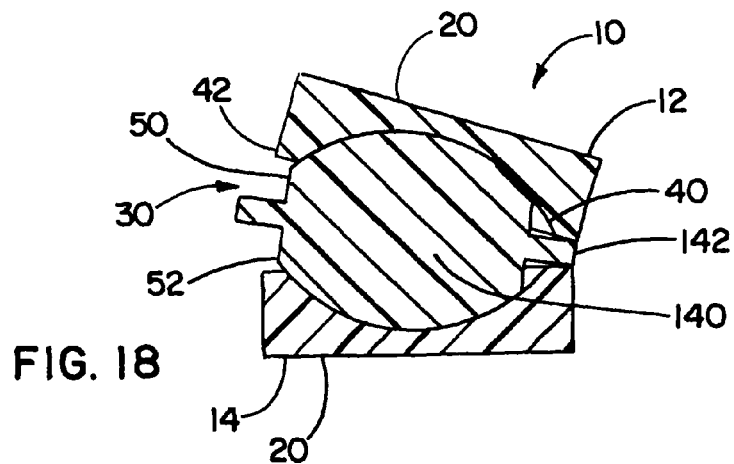
FIG. 18 is a cross-sectional view of an implant with a spacer member having a peripheral structure for restricting motion of the shells in the anterior-posterior direction.
Figure 19:
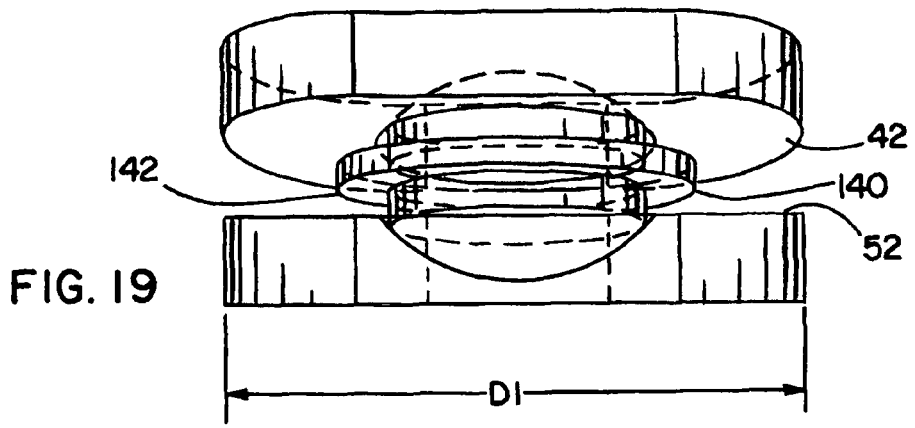
FIG. 19 is a perspective view of the implant of FIG. 18.

As discussed previously, the greatest angle of deflection between vertebrae in a natural disc is approximately 15°. The extended lateral dimension D1 of the shells 12, 14 restricts the lateral bending to 15°. However, it may be necessary to restrict the anterior-posterior bending of the implant 10. As can be seen in FIGS. 16-17, the shells 12, 14 include short walls 130 that oppose and extend toward each other such that the walls 130 abut when a 15° bend is reached. Alternatively, as can be seen in FIGS. 18-19, a spacer member 140 may include an annular ring 142 extending from its periphery and between the shells 12, 14 such that the faces 42, 52 of the top and bottom shells 12, 14 contact the ring 142 when the 15° angle is reached. The ring 142 may be made of a softer material than that of the shells 12, 14 to minimize wear, and may be resiliently compressible. The short walls 130 and the dimension of the ring 142 may be sized to provide or restrict motion of the shells 12, 14 to an angle, such as 15E or another angle, as desired.

Figure 20:
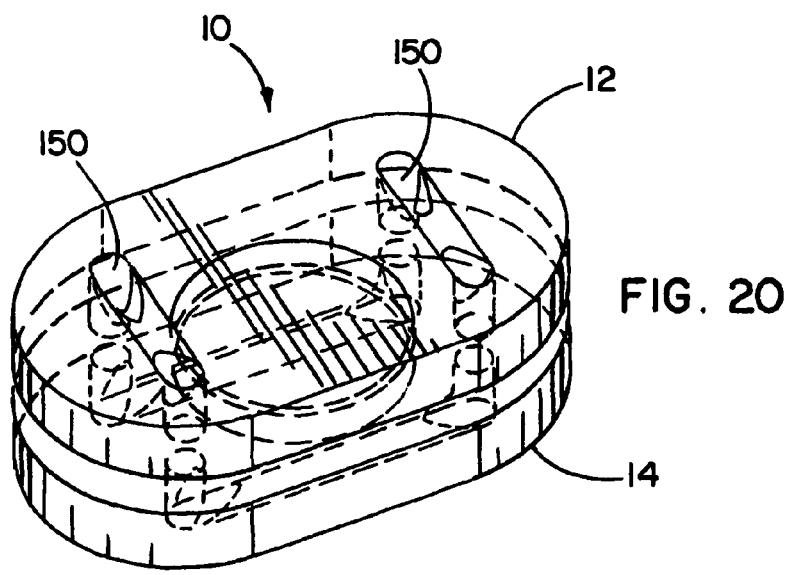
FIG. 20 is a perspective view of an implant having channels for a cable to restrict motion of the shells.
Figure 21:
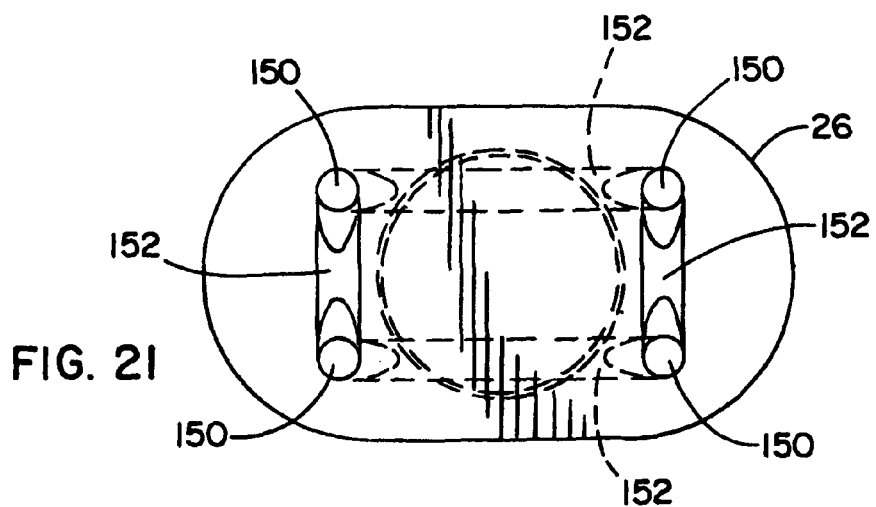
FIG. 21 is a top plan view of the implant of FIG. 20.
Figure 22:
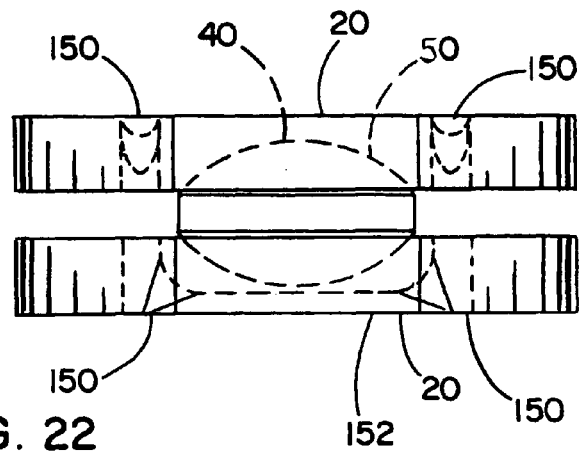
FIG. 22 is a side elevational view of the implant of FIG. 20.

In an alternative embodiment depicted in FIGS. 20-22, each shell 12, 14 includes two pairs of ports 150, each port 150 generally aligned with a port 150 of the opposing shell 12, 14 and each pair including a channel 152 recessed in the outer surface 20 of the shell 12, 14 to connect the pair. A cable (not shown) may be threaded through the ports 150 and through the channels 152 so as to be recessed from the outer surfaces 20 of the shells such that the cable forms a closed loop. In this manner, the sides of the shells 12, 14 opposite the direction of bending can only be separated to a degree provided by the length of the cable. The cable is provided with length such that the degree of separation between the shells 12, 14 does not exceed 15°, or any other angle, in the anterior-posterior direction. Furthermore, the cable arrangement prevents the shells 12, 14 from separating from each other and blocks the space between the shells 12, 14 so that the spacer member 60 therebetween cannot come loose and escape from between the shells 12, 14.

Figure 23:
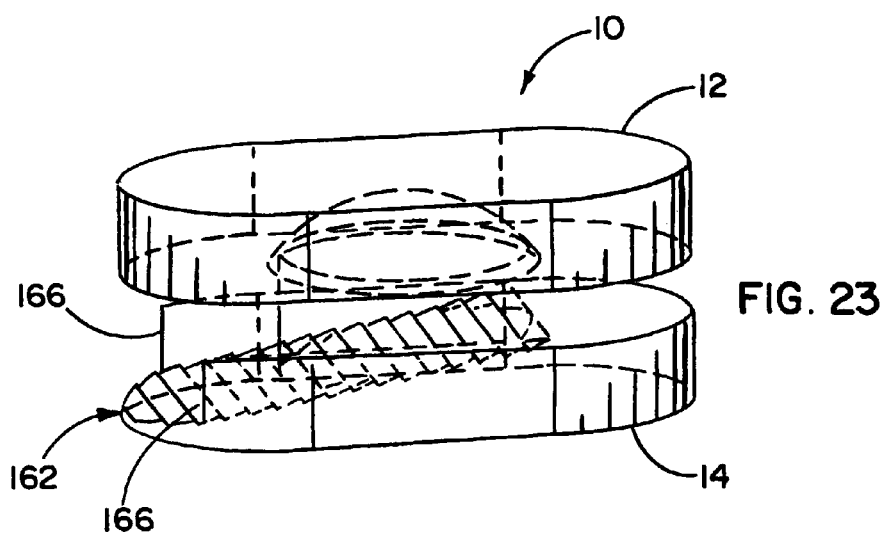
FIG. 23 is a perspective view of an implant and a spacer member in partial phantom.
Figure 24:
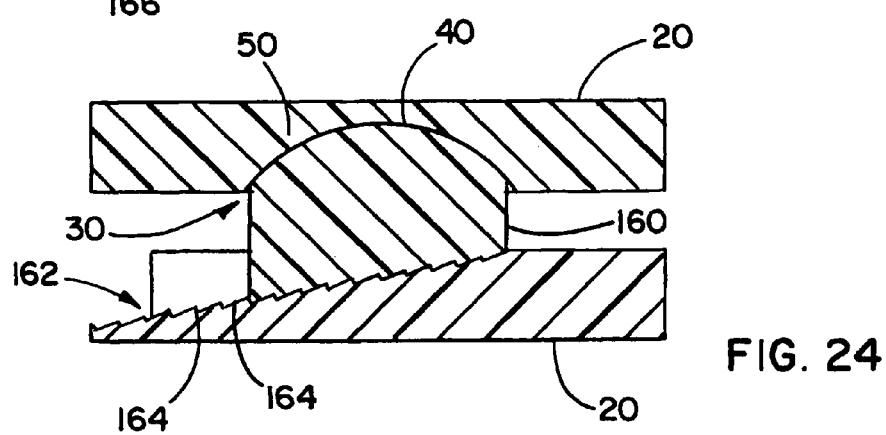
FIG. 24 is a cross-sectional view of the implant of FIG. 23.
Figure 25:
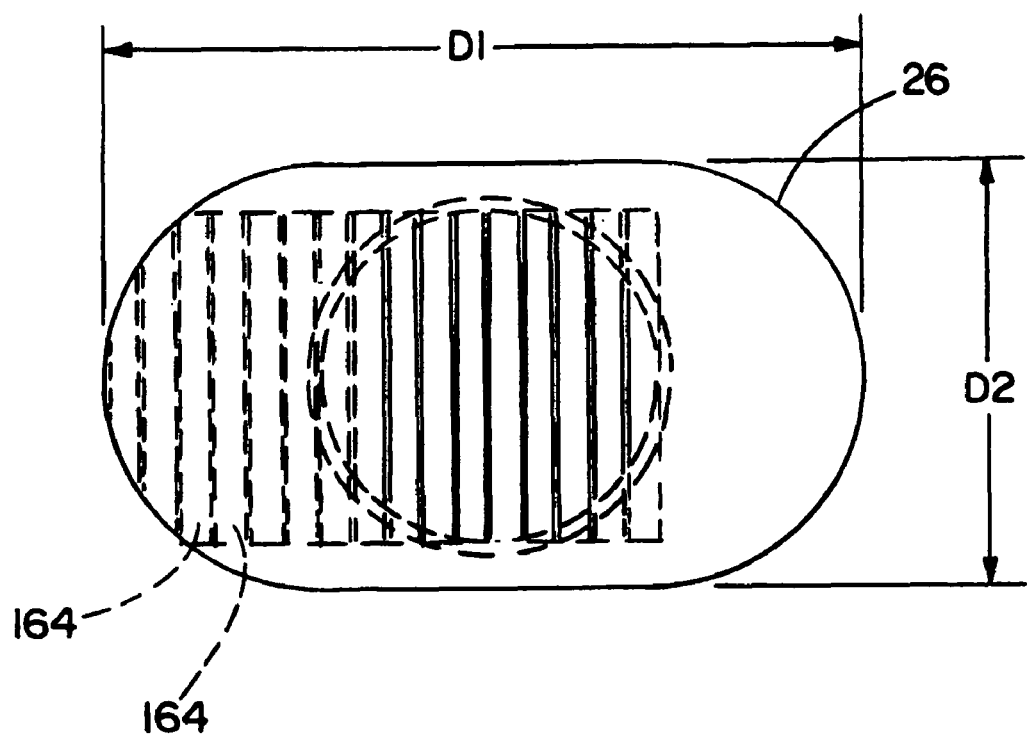
FIG. 25 is a top plan view of the implant of FIG. 23 in partial phantom.

Referring now to FIGS. 23-25, an implant 10 is depicted having top and bottom shells 12, 14 and a stepped spacer member 160. The bottom shell 14 includes an inclined stepped ramp 162 with, preferably, steps 164 aligned in the anterior-posterior direction and sidewalls 166 to the sides of the steps 164. The steps 164 rise toward the center of the shell 14, and a dome surface 50 on the opposite side of the spacer member 160 contacts and is received in a recess 40. The shells 12, 14 may be inserted in the nucleus space with the stepped ramp 162 aligned with the incision in the annulus. In one form, the dome surface 50 of the spacer member 160 may cam against the top shell 12 while being forced between the shells 12, 14 and into the nuclear space. The stepped spacer member 160 may be forced between the shells 12, 14 so that the stepped spacer member 160 cams against and ratchets up the steps 164. The sidewalls 166 are positioned so that the spacer member 160 may slide or translate a short distance in the anterior-posterior direction along the steps, while also preventing overtranslation. Once the stepped spacer member 160 is inserted, the stepped shell 14 may be rotated so the ramp 162 is no longer aligned with the incision of the annulus. To prevent the spacer member 160 from repositioning to a lower portion of the stepped ramp 162 once implanted, a stop (not shown) may be provided, or the steps 164 may be canted such that each step 164 is angled downward toward the inboard edge of the step 164, and the steps 164 and the bottom surface of the stepped spacer member 160 interlock, as is depicted. Alternatively, the bottom shell 14 including the stepped ramp 162 may be inserted, and then the spacer member 160 and the top shell 12 may be inserted together with the dome surface 50 received in the concave recess 40. Accordingly, both the spacer member 160 and the top shell 12 are forced into the nuclear cavity such that the spacer member 160 ratchets up the steps 164 of the bottom shell 14. As a further alternative, the top and bottom shells 12, 14 and the stepped spacer member 160 may be inserted together with the spacer member 160 positioned at the lower steps 164 to the implant has a reduced size or thickness during insertion into the nuclear cavity.

Figure 26:
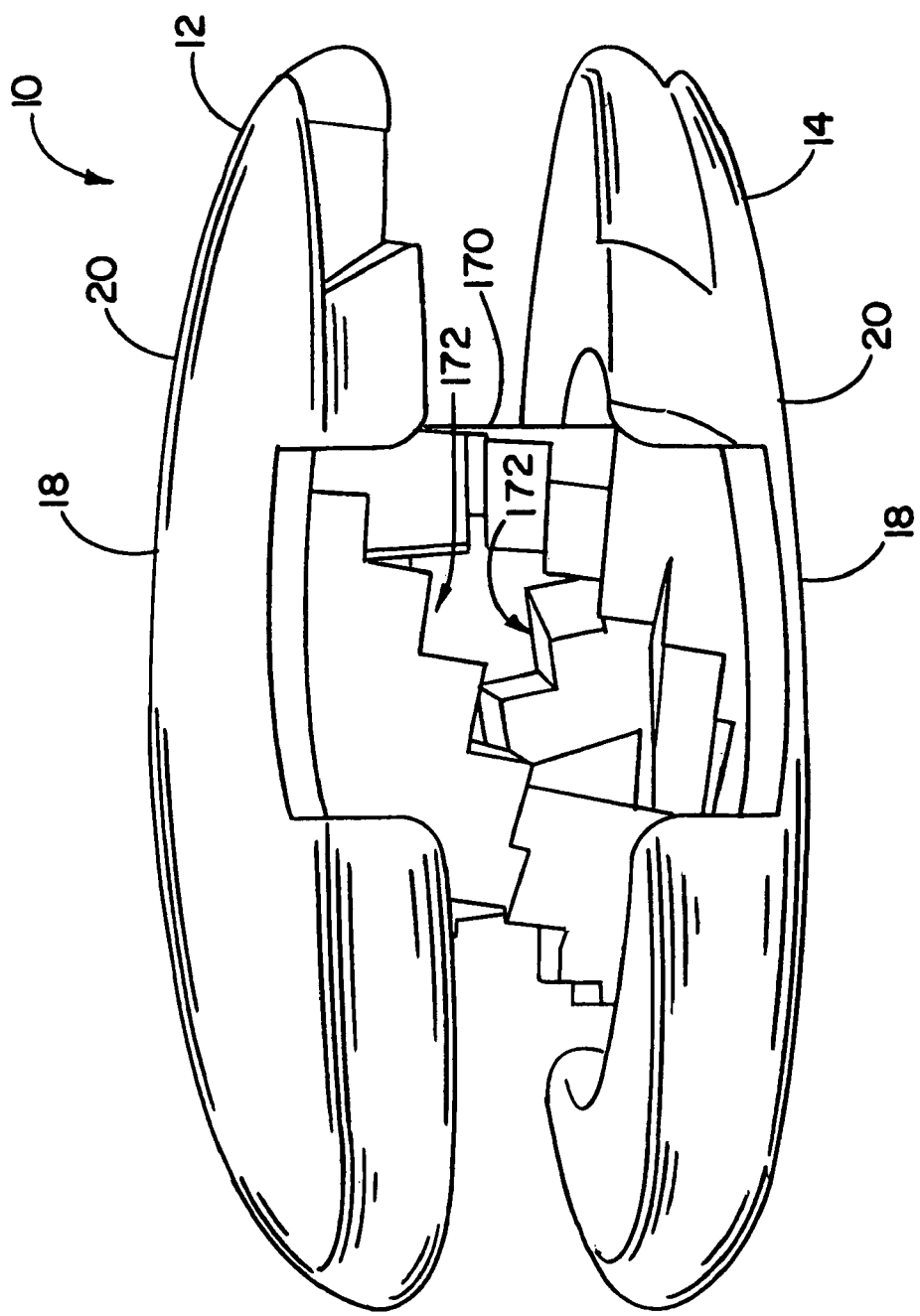
FIG. 26 is a perspective view of an implant having a helical insert.
Figure 27:
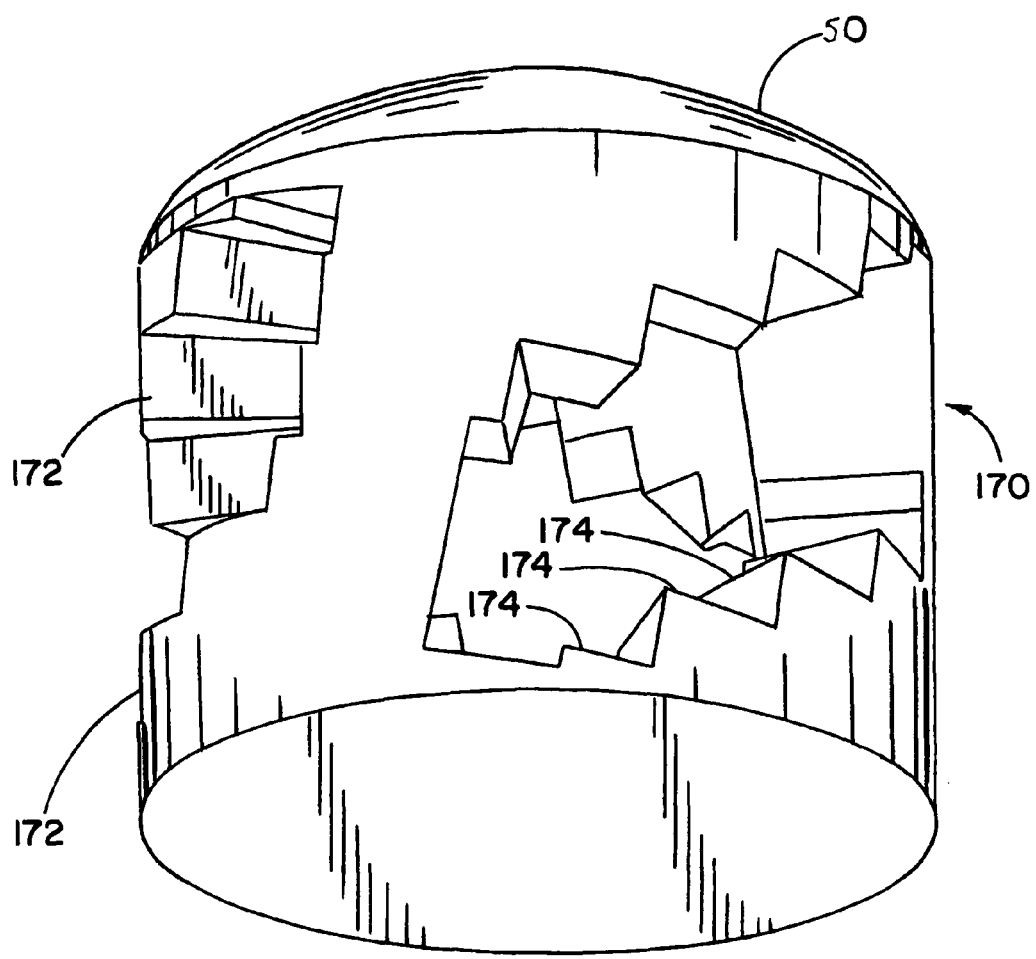
FIG. 27 is a perspective view of the helical insert of FIG. 26.

Referring to FIGS. 26-27, an implant 10 inserted in a collapsed or compressed state or arrangement and then expanded is depicted having top and bottom shells 12, 14 and a helically stepped spacer member 170. Both shells 12, 14, but preferably one shell 12, 14, have a concave recess 40 into which a dome surface 50 formed on the spacer member 170 is received. The spacer member 170 has two opposing stepped helical wall sections 172. In some forms, one of the helical walls sections 172 is integral with one of the shells 12, 14, while in other forms both helical wall sections 172 include a dome surface 50 received by a concave recess 40 in the respective mating shells 12, 14. The helical wall sections 172 have opposing helically arranged steps 174. The implant 10 is inserted into or assembled within the nucleus in a compressed arrangement with the helical wall sections 172 fully intermeshed with each other. Once inserted, the helical wall sections 172 may be rotated relative to each other such that the opposing steps 174 of the helical wall sections 172 ratchet against each other and thereby expand the implant 10 to an expanded arrangement. The implant 10 may be constructed to prevent undesired repositioning of the helical wall sections 172. Similarly to the implant 10 described above having a stepped ramp 162, the steps 174 of the helical wall sections 172 may be canted forward in the direction of rotation for expansion to prevent or impede repositioning, or a stop (not shown) may be provided. As a further alternative, the implant 10 may be provided with a compression and/or torsional spring (not shown) so that, once implanted, the helical wall sections 172 are automatically forced open and rotated to an expanded arrangement, and the helical wall sections 172 may then hold the shells 12, 14 in the expanded arrangement.

Figure 28:
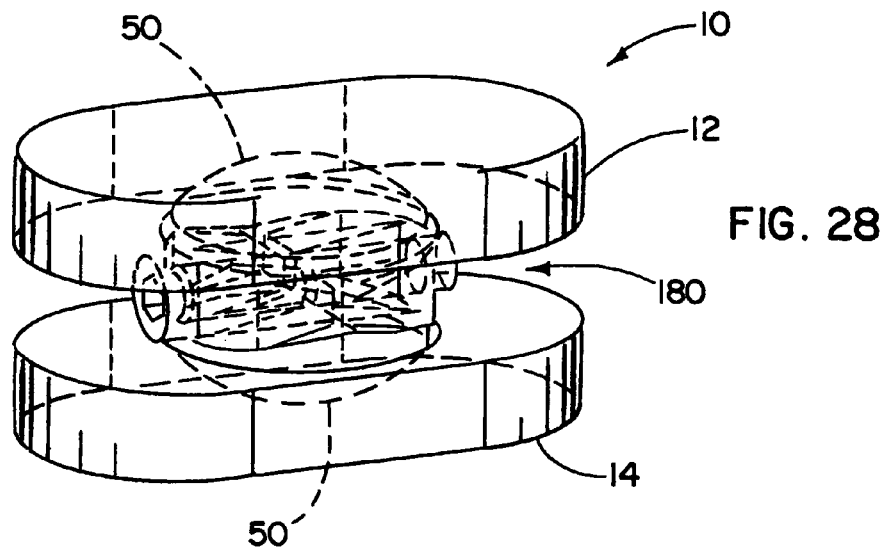
FIG. 28 is a perspective view of an implant having a rotational member for directing wedges.
Figure 29:
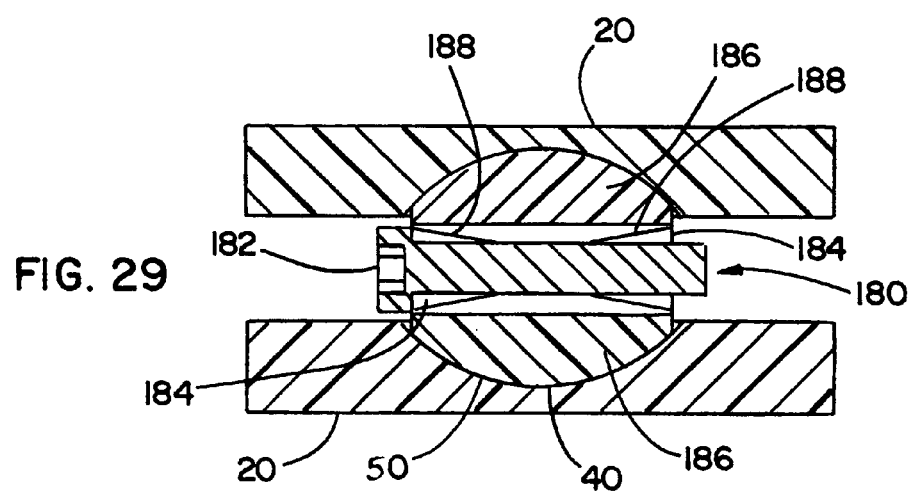
FIG. 29 is a cross-sectional view of the implant of FIG. 28.
Figure 30:
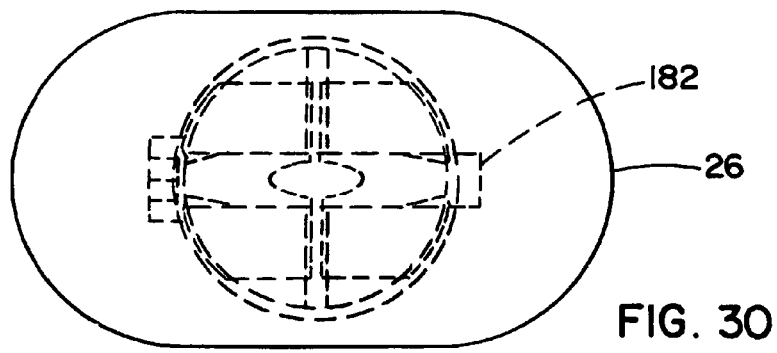
FIG. 30 is a top plan view of the implant of FIG. 28 in partial phantom.

As a further alternative, FIGS. 28-30 depict an implant 10 having top and bottom shells 12, 14, and a spacer member 180 which includes a rotating member 182 that rotates around its longitudinal axis connected to a pair of opposed wedges 184 and a pair of hemispherical members 186. Each hemispherical member 186 includes a dome surface 50 received within a recess 40 in the respective shell 12, 14. The rotating member 182 is threaded within the wedges 184. Turning the rotating member 182 in a particular direction forces the wedges 184 from a compressed arrangement where the wedges 184 are separated to an expanded arrangement with the wedges 184 closer together or abutting each other. The wedges 184 in the compressed arrangement are generally positioned laterally to a space 186 between the hemispherical members 186. Turning the rotating member 182 to draw the wedges 184 closer pulls the wedges 184 to a position within the space 186. In doing so, wedge surfaces 188 abut the hemispherical members 186, thereby forcing the hemispherical members 186 away from each other and forcing the implant to the expanded arrangement. The implant 10 may be inserted in the compressed arrangement, and then expanded as described. As alternatives, a single wedge may be utilized with a rotating member rotationally secured (not shown) to either a shell or a hemispherical member, or the wedges may expand the implant by being forced outward, away from each other, as opposed to being forced inward, as described. It is preferred that an end of the rotating member 182 used to effect its rotation is positioned to face the incision during its rotation.

Figure 31:
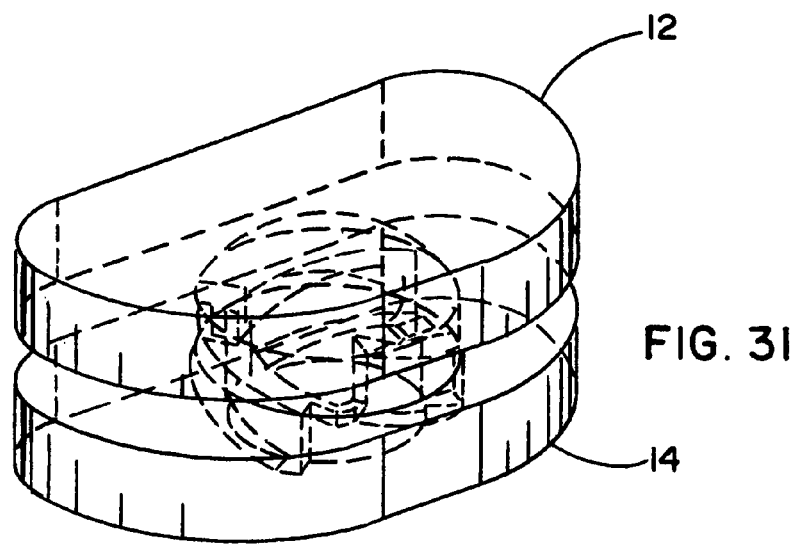
FIG. 31 is a partial phantom perspective view of an implant with a camming spacer member.
Figure 32:
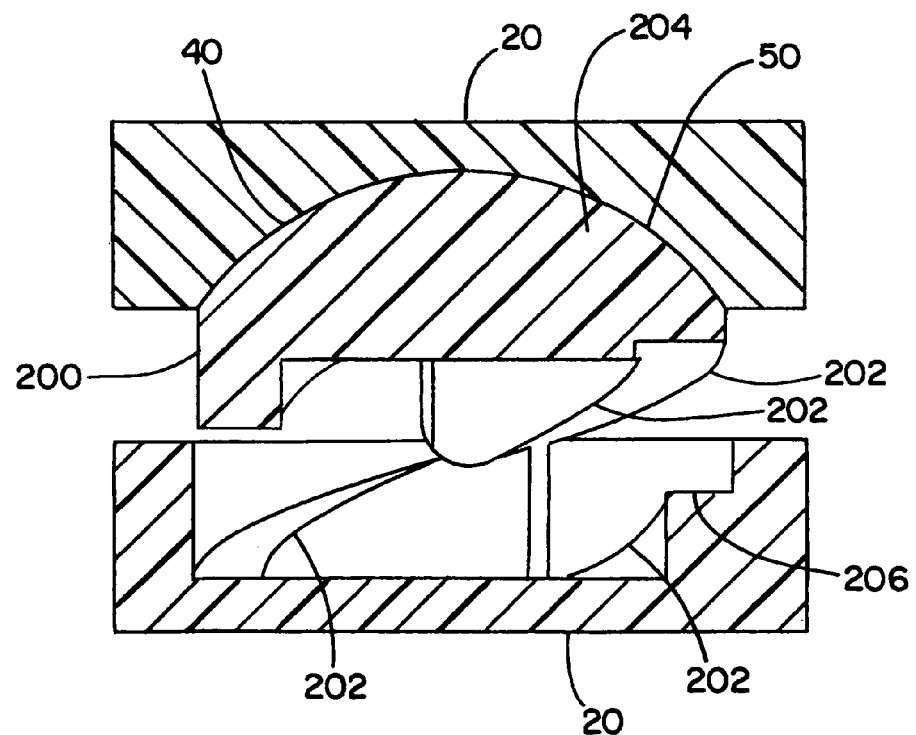
FIG. 32 is a cross-sectional view of the implant of FIG. 31.

Referring now to FIGS. 31-32, an implant 10 is depicted having a spacer in the form of cam member 200 with cam surfaces 202 such that the implant 10 may be in inserted in a compressed arrangement, and the cam surfaces 202 may then rotate to expand the implant 10. The cam member 200 includes a camming dome 204 having a dome surface 50 received in a recess 40 in the top shell 12. The camming dome 204 preferably has three or more cam surfaces 202 mating with opposed cam surfaces 202 of the bottom shell 14. In the compressed or unexpanded arrangement, the cam surfaces 202 of the camming dome 204 and bottom shell 14 are fully interlocked and intermeshed. The camming dome 204 may be rotated relative to the bottom shell 14 such that the mating cam surfaces 202 cam against each other, thereby forcing the camming dome 204 up and expanding the implant 10 from a compressed arrangement to an expanded arrangement. At the highest point 206 of the cam surfaces 202 of the bottom shell 14, there is a hump or other stop, beyond which the cam surfaces 202 may seated to prevent the camming dome 204 from repositioning to a lower level. Alternatively, a pair of camming domes 204 may be provided with cam surfaces 202 therebetween such that the camming domes 204 may be rotated relative to each other to expand the implant 10.

Figure 33:
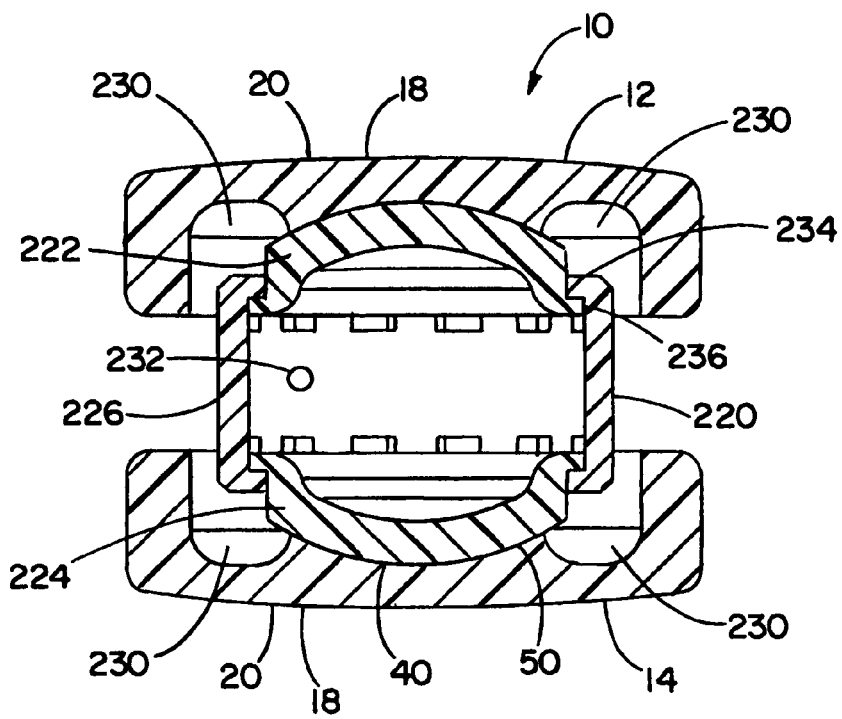
FIG. 33 is a cross-sectional view of a first implant with an expandable cannister.
Figure 34:
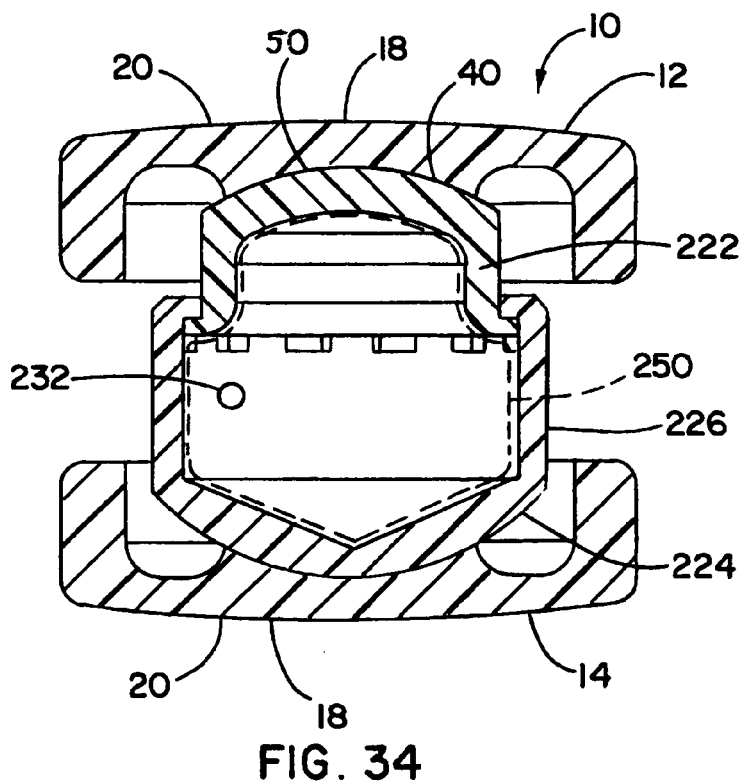
FIG. 34 is a cross-sectional view of a second implant with an expandable cannister.

In an alternative embodiment of the expandable implant, FIGS. 33-34 depict implants 10 with top and bottom shells 12, 14 and an expandable cannister. In FIG. 33, a cannister 220 has a top cap 222, a bottom cap 224, and a sidewall 226. The top cap 222 and bottom cap 224 each have a dome surface 50 mating with a recess 40 on respective shells 12, 14. The implant 10 is inserted in the nucleus space in a compressed or unexpanded arrangement, and the shells 12, 14 have annular recesses 230 for receiving the sidewall 226 when the implant 10 is in the compressed arrangement. The sidewall 226 includes an inlet 232 so that the cannister 220 may be expanded by injecting the cannister 220 with a flowable material, thereby expanding the implant 10 to the expanded arrangement. The sidewall 226 has an inwardly extending lip 234 on its top and bottom edge which interferes with an outwardly extending lip 236 on each of the caps 222, 224 when the cannister 220 is fully expanded. Referring to FIG. 34, an alternative cannister 240 is depicted where the bottom cap 224 is integral with the sidewall 226. The cannister 220 may preferably be filled with a curable material so that the material does not leak from the expanded cannister 220. In these embodiments, the caps 222, 224 should form a sufficient seal with the sidewall 226 so that the material is retained within the cannister 220, 240. As an alternative, one of the caps 222, 224 may be integral with one of the shells 12, 14.

Alternatively, the cannister 220 may be filled with fluid, or may be filled with elastomeric material so that the cannister 220, 240 provides some degree of shock absorption. As a further alternative, a balloon 250 may be used instead of the cannister 220, 240. If only a balloon is used, a deflated balloon may be pre-positioned within the shells 12, 14 when the implant 10 is inserted in the nuclear space, or a deflated balloon may be inserted after the shells are implanted. In order to fill the balloon 250, it should have a port or inlet aligned with the inlet 232 in the sidewall 226 for receiving the injected material from, for instance, a catheter. When the catheter, for instance, is removed after filling the implant, the balloon or cannister should be sealed. Accordingly, it is preferred that a self-sealing valve or valve-less connection is made between the injection device and the balloon or cannister. Alternatively, the injected material may seal the balloon or cannister, such as when the material is curable. When a balloon is used with the sidewall 226, the function of the sidewall 226 is to limit or reduce the lateral deformation of the balloon so that the height of the implant 10 is maintained.

If a balloon 250 is used without being enclosed and generally immobilized in another structure and is filled with a non-curable material, a non-compliant or minimally compliant balloon may be used to maintain rigidity during physiological loading. The balloon may be filled with, as examples, saline, silicone oil, or PEG solution. If the balloon is filled with curable material, the balloon may be formed of both compliant and non-compliant material. Suitable curable materials include but are not limited to, as examples, PMMA, calcium phosphate, polyurethane, and silicone.

In some forms, of the expandable implant, the ability to control the degree of expansion is provided. For instance, the wall sections 172 of the helical stepped spacer member 170 may be rotated to a desired height, or the expansion of the cannister 220 may be controlled by controlling the amount of injected material. Both the height or expansion of the implant 10 and the distraction force on the vertebrae may be monitored and controlled. However, it is preferred from a clinical standpoint to expand the implant 10 to a pre-determined distraction force so the expansion is performed with respect to contact pressure on the end plate of the vertebrae.

Each polyaxial bearing member 30 as described herein has an outer contour mating with a similar shaped recess. Though the outer contour of the dome surface may be a partial spheroid, hemispherical, or similar structure, it should be noted that other shapes, such as oblong or parabolic, may offer greater function. Alteration of the shape of the dome surface may be utilized to provide different ranges of motion to the polyaxial bearing member 30. As depicted, the spacers have one or two arcuate dome surfaces with radii of curvature that, if they were to form a complete spheroid, would be prohibitively large for use in the intervertebral space. Alternatively, a spacer member may be provided as a rigid ball or semi-rigid arcuate ball.

Advantageously, the dome surface and recess bearing member 30 produces an interface between the shell and the spacer member that allows greater freedom for the shells to be relatively oriented when implanted. Specifically, the shells may orient in a wedge angle appropriate for various intervertebral disc levels. For instance, at different levels, such as the L5/S1 level, the vertebrae are oriented in a wedge angle for maintaining a lordotic shape in the spine. With the free rotation of the shells against the ball, the shells may angularly adjust in accordance with the natural curvature of the spine without creating uneven stress distributions on the end plates of the vertebrae.

Materials for the shells 12, 14, and any spacer such as spacer member 60 may be selected to provide certain properties. Materials may be selected to provide desirable wear characteristics between sliding surfaces, and may be selected to provide radiotranslucency. In any event, the materials for the shells 12, 14, and any components of the articulating bearing member 30 are generally rigid so that the implant 10 is capable of supporting the cyclic compressive loads experienced by the implant 10, as a natural disc would experience. Some examples of materials are metals, ceramics, plastics, composite materials and elastomers. Metals may include surgical grade stainless steel, Co—Cr alloys, liquid metal, titanium, and titanium alloys. Ceramics may include alumina, and zirconia. Plastics may include polyethylene, polypropylene, pyrolytic carbon, PEEK™, and BioPEKK™. Composites may include carbon fiber PEEK and carbon fiber BioPEKK. Elastomers may include polyurethane. Non-metallic materials benefit from being radiolucent and from not causing artifact during imaging, such as radiographic, magnetic resonance, or CAT scan. With non-metallic materials, it may be beneficial to include a radio opaque marker in the device to assist in identification in an image. It should be realized that the above-named materials are only examples, and this is not an attempt to catalog a complete list of materials which may be used.

The spacer member and the shells may be made from matching material, or may be made from different materials. Generally, use of a non-metallic material for the shell would benefit from using a non-metallic material for the spacer member to avoid artifact during imaging. However, use of a metallic material on the wear surfaces may improve the wear resistance on the articulating and sliding surfaces.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

The invention claimed is:

1. A two-part prosthetic spinal nucleus device for replacing a nucleus of a spinal disc and being implanted in an intervertebral space within a natural annulus and between natural end plates attached to adjacent axially spaced upper and lower vertebral bones, the device comprising:

a rigid upper shell having a one-piece elongate body having a predetermined length between opposite narrow ends and a predetermined width between opposite elongate sides and including a smooth outer surface having a flat configuration extending substantially entirely across the length and width of the shell for facing and non-invasively contacting the natural end plate of the upper vertebra for sliding engagement therewith and sized to fit within the natural annulus of the spinal disc;

a rigid lower shell having a one-piece elongate body having a predetermined length between opposite narrow ends and a predetermined width between opposite elongate sides and including a smooth outer surface having a flat configuration extending substantially entirely across the length and width of the shell for facing and non-invasively contacting the natural end plate of the lower vertebra for sliding engagement therewith and sized to fit within the natural annulus of the spinal disc;

inner, arcuate bearing surfaces of the one-piece bodies of the upper and lower shells that are in sliding engagement with each other including a dome-shaped inner bearing surface of one of the shell bodies having truncated, diametrically opposite edge portions that extend along the opposite elongate sides of the one shell body such that a diameter of the dome-shaped inner bearing surface is longer than the width of the one shell body and the dome-shaped inner bearing surface extends substantially across the entire width of the one shell body between the opposite edge portions; and the elongate sides of each of the shell bodies extending lengthwise between the narrow ends thereof so that the sides are longer than the width across the narrow ends to allow the shells to be arranged with narrow ends of the shell bodies leading the shells as the shells are inserted through an incision smaller than the elongated sides of the shell bodies so that the natural annulus retains the shells in the intervertebral space with the smooth outer surfaces of the shell bodies extending continuously without interruption across the entire extent of the length and the width thereof between the ends and sides of the respective shell bodies.

2. The device of claim 1 wherein the shell bodies are configured to be sequentially inserted through the incision in the annulus, and be assembled within the annulus.

3. The device of claim 1 wherein at least one of the shells includes a gripping projection integral with the body of the one shell configured to allow a separate tool to grip around the projection for tool insertion of the shells through the annulus incision into the invertebral space and shifting of the shells therein so that the narrow shell ends are not aligned with an insertion direction of the shells through the incision.

4. The device of claim 3 wherein the gripping projection comprises a gripping post of the at least one of the upper and lower shells that projects from the one shell toward the other of the upper and lower shells.

5. The device of claim 3 wherein the gripping projection includes an arcuate engagement surface for rotating the one shell with the tool, and a generally flat abutment surface for locking the one shell against rotation with the tool.

6. The device of claim 1 wherein the inner, arcuate bearing surfaces comprise engaging concave and convex bearing surfaces of the upper and lower shell bodies that bear against each other for substantially the entire arcuate extent thereof without discontinuities in the bearing surfaces.

7. The device of claim 6 wherein the shell bodies include flat surface portions adjacent the concave and convex bearing surfaces.

8. The device of claim 7 wherein the flat surface portion of one of the shell bodies includes an integral gripping post projecting away therefrom.

9. The device of claim 1 wherein one of the shell bodies includes a flat surface portion and the inner bearing surface of the one shell body is a concave surface portion recessed from the flat surface portion, and the other shell body includes a flat surface portion and the inner bearing surface of the other shell body is the dome-shaped inner bearing surface projecting beyond the flat surface portion of the other shell body.

10. The device of claim 1 wherein the bodies of the rigid upper shell and the rigid lower shell are entirely of a polyetheretherketone (PEEK) material so that the PEEK inner bearing surfaces bear and articulate against each other and provide optimized wear resistance and cyclic load bearing capacity upon being implanted in the intervertebral space in the annulus.

11. A nucleus implant device for replacing a nucleus of an intervertebral spinal disc leaving the natural spinal annulus and end plates of adjacent upper and lower vertebrae intact, the nucleus implant device comprising:

an upper load bearing member having a width between opposite sides thereof for being implanted in an intervertebral space within the intact, natural annulus adjacent the upper vertebra;

a lower load bearing member having a width between opposite sides thereof for being implanted in the intervertebral space within the intact, natural annulus adjacent the lower vertebra;

a polyetheretherketone (PEEK) material of both the upper load bearing member and the lower load bearing member so that the load bearing members are of matching material;

PEEK outer bearing surfaces of the matched PEEK load bearing members having a smooth, flat configuration for substantially the entire extent thereof so as to lack any protrusions projecting outwardly therefrom for non-invasive sliding engagement with the corresponding intact, natural end plates; and PEEK inner bearing surfaces of the matched PEEK load bearing members each having an arcuate configuration including a dome-shaped inner bearing surface of one of the PEEK load bearing members having truncated surface portions substantially coincident with the opposite sides of the one bearing member such that the truncated surface portions extend from the dome-shaped inner bearing surface along the opposite sides of the one bearing member such that a diameter of the dome-shaped inner bearing surface is longer than the width of the one bearing member and the dome-shaped inner bearing surface extends substantially across the entire width of the one bearing member, and a corresponding arcuate recess-shaped inner bearing surface of the other of the PEEK load bearing members configured to cooperate with the dome-shaped inner bearing surface and together allow for polyaxial rotation and sliding of the matched PEEK load bearing members relative to each other so that there are multiple PEEK outer bearing interfaces and a PEEK-on-PEEK inner bearing interface with the PEEK outer surfaces of the load bearing members forming the multiple PEEK outer bearing interfaces and the PEEK inner surfaces of the load bearing members forming the PEEK-on-PEEK inner bearing interface to allow for differential shifting of the different PEEK bearing interfaces optimizing wear resistance thereof and cyclical load capacity provided thereby.

12. The nucleus implant device of claim 11 wherein the arcuate inner bearing surfaces comprise the dome-shaped inner bearing surface and the corresponding arcuate recess-shaped inner bearing surface for receiving the dome-shaped inner bearing surface in engagement therewith each engaging inner bearing surface being uninterrupted the entire extent thereof for smooth, continuous bearing engagement therebetween.

13. The nucleus implant device of claim 11 wherein at least one of the load bearing members has a post configured to be engaged by a tool for implanting at least the one load bearing member in the intervertebral space.

14. The nucleus implant device of claim 13 wherein both load bearing members include posts for a tool, and the arcuate inner bearing surfaces comprise the dome-shaped inner bearing surface and the corresponding arcuate recess-shaped inner bearing surface sized such that with the dome-shaped inner bearing surface engaged in the corresponding arcuate recess-shaped inner bearing surface, the posts aligned with each other, and plate bodies of the load bearing members generally extending in parallel to each other, a predetermined gap spacing is provided between free ends of the aligned posts to avoid significant interference with the relative movement between the load bearing members at the inner bearing interface.

15. The nucleus implant device of claim 11 wherein the load bearing members each have an elongated configuration with opposite narrow ends and long sides extending between the narrow ends allowing an incision in the annulus to be kept to a minimum size with the load bearing members inserted therethrough with the narrow ends leading the members through the incision.

16. The nucleus implant device of claim 11 wherein the load bearing members include bodies that are entirely of the PEEK material including the bearing surfaces thereof less any radio opaque markers included in the PEEK bodies.

17. The device of claim 1, wherein the outer bearing surfaces are substantially race-track shaped for allowing the bearing members to fit within the natural annulus.

18. The device of claim 1, wherein the narrow ends of the shells each have an arcuate configuration and the elongate sides extend parallel to one another between the narrow ends.

19. The device of claim 1, wherein the smooth outer surfaces of the shells are entirely free of bone-engaging protrusions or surface roughening to promote sliding engagement of the bearing members with the end plates such that the nucleus device is allowed to move freely along the endplates within the annulus.

20. The device of claim 1, wherein the truncated, diametrically opposite edge portions of the dome-shaped inner bearing surface extend substantially parallel to a longitudinal axis of the one shell body.

* * * * *